(12) United States Patent
Greene et al.

(10) Patent No.: US 12,090,130 B2
(45) Date of Patent: Sep. 17, 2024

(54) METHODS OF TREATING BRAIN DISORDERS

(71) Applicants: Neuronasal, Inc., Wexford, PA (US); Burke Neurological Institute, White Plains, NY (US)

(72) Inventors: Douglas A. Greene, Basking Ridge, NJ (US); Rajiv R. Ratan, White Plains, NY (US); Thomas I. Bradshaw, Wynnewood, PA (US)

(73) Assignees: Neuronasal, Inc., Wexford, PA (US); Burke Neurological Institute, White Plains, NY (US)

( * ) Notice: Subject to any disclaimer, the term of this patent is extended or adjusted under 35 U.S.C. 154(b) by 443 days.

(21) Appl. No.: 17/127,075

(22) Filed: Dec. 18, 2020

(65) Prior Publication Data
US 2021/0186911 A1    Jun. 24, 2021

Related U.S. Application Data

(60) Provisional application No. 62/970,254, filed on Feb. 5, 2020, provisional application No. 62/949,640, filed on Dec. 18, 2019.

(51) Int. Cl.
*A61K 31/198* (2006.01)
*A61K 9/00* (2006.01)

(52) U.S. Cl.
CPC .......... *A61K 31/198* (2013.01); *A61K 9/0043* (2013.01); *A61K 9/0075* (2013.01); *A61K 9/0078* (2013.01)

(58) Field of Classification Search
CPC .. A61K 31/198; A61K 9/0043; A61K 9/0075; A61K 9/0078
USPC ...................................................... 514/561
See application file for complete search history.

(56) References Cited

U.S. PATENT DOCUMENTS

| | | |
|---|---|---|
| 2009/0234011 A1 | 9/2009 | Goldstein |
| 2010/0292512 A1 | 11/2010 | DiMauro |
| 2015/0148423 A1 | 5/2015 | Goldstein |
| 2016/0058726 A1 | 3/2016 | Cohen |
| 2018/0161297 A1 | 6/2018 | Kirnon et al. |
| 2018/0344678 A1 | 12/2018 | Ratan et al. |

FOREIGN PATENT DOCUMENTS

| | | |
|---|---|---|
| WO | WO-2019084543 A1 | 5/2019 |

OTHER PUBLICATIONS

Borgstrom, L. et al., Pharmacokinetics of N-Acetylcysteine in Man, European Journal of Clinical Pharmacology, (1986) 31: 217-222.
Borgstrom, Lars et al., Dose Dependent Pharmacokinetics of N-Acetylcysteine After Oral Dosing to Man, Biopharmaceutics& Drug Disposition, (1990) vol. 11, 131-136.
Burke, Matthew et al., In search of evidence-based treatment for concussion: characteristics of current clinical trials, Brain Injury, 2015; 29(3): 300-305.
CPSTechnology Platform, Dec. 2016—version 1, pp. 1-4, aptar. com/pharma.
Eakin, Katharine et al., Efficacy of N-Acetyl Cysteine in Traumatic Brain Injury, PLOS One, Apr. 2014, vol. 9, issue 4, e90617.
Elahi, Morvarid et al., The Effects of N-Acetyl Cysteine on Nasal Mucociliary Clearance in Healthy Volunteers: A Randomized, Double-Blind and Placebo-Controlled Study, Otolaryngology 2015, 5:1, http://dx.doi.org/10.4172/2161-119X.1000182.
Hicdonmez, Tufan et al., Neuroprotective Effects of N-acetylcysteine on Experimental Closed Head Trauma in Rats, 2006, Neurochem Res 31:473-481, DOI 10.1007/s11064-006-9040-z.
Highlights of Prescribing Information, ACETADOTE(acetylcysteine) Injection, Initial U.S. Approval: 2004, Package Insert, pp. 1-8, Revised: Jun. 2013.
Hoffer, Barry J. et al., Repositioning drugs for traumatic brain injury—N-acetyl cysteine and Phenserine, Journal of Biomedical Science (2017) 24:71, pp. 1-15,DOI10.1186/s12929-017-0377-1.
Hoffer, Michael E. et al., Amelioration of Acute Sequelae of Blast Induced Mild Traumatic Brain Injury by N-Acetyl Cysteine: A Double-Blind, Placebo Controlled Study, PLOSONE, Jan. 2013, vol. 8, Issue 1, e54163.
Holdiness, Mack R., Clinical Pharmacokinetics of N-Acetylcysteine, Clin. Pharmacokinet. 20 (2): 123.134.1991.
Input on Usability and Human Factors for Aptar Cps Pump System, Aptar Pharma, 2 pages, 2016.
International Search Report and Written Opinion dated Jan. 7, 2021 for International Application Serial No. PCT/US2020/058905 , (9 pages).
International Search Report and Written Opinion dated Mar. 9, 2021 for International Application Serial No. PCT/US2020/066179, (8 pages).
Kawoos, Usmah et al., N-acetylcysteine Amide Ameliorates Blast-Induced Changes in Blood-Brain Barrier Integrity in Rats, Jun. 2019, Frontiers in Neurology, vol. 10, article 650, pp. 1-7.
Kawoos, Usmah et al. ,Protective Effect of N-Acetylcysteine Amide on Blast-Induced Increase in Intracranial Pressure in Rats, Jun. 2017, Frontiers in Neurology, Jun. 2017, vol. 8, article 219, pp. 1-8.
Macchi, A. et al., Recurrent Acute Rhinosinusitis: A Single Blind Clinical Study of N-Acetylcysteine Vs Ambroxol Associated To Corticosteroid Therapy, 2012, International Journal of Immunopathology and Pharmacology, vol. 25, No. 1, pp. 207-217.
Mischley, L., Conley, K., Shankland, E. et al., Central nervous system uptake of intranasal glutathione in Parkinson's disease, Nature Partner Journals, Parkinson's Disease 2, 16002 (2016), pp. 1-6. https://doi.org/10.1038/npjparkd.2016.2.
Mischley, ND, MPH, PhD(c), Laurie K. et al., A Randomized, Double-Blind Phase I/IIa Study of Intranasal Glutathione in Parkinson's Disease, 2015, Movement Disorders, vol. 30, No. 12, pp. 1695-1701.

(Continued)

*Primary Examiner* — Kristin A Vajda
(74) *Attorney, Agent, or Firm* — Frost Brown Todd LLP

(57) ABSTRACT

The present disclosure describes methods of administering N-acetylcysteine (NAC) via intranasal nose-to-brain administration. The effect of intranasal NAC nose-to-brain administration can be monitored using an analytical technique, for example, magnetic resonance spectroscopy (MRS). In some embodiments, intranasal nose-to-brain NAC can be used to treat a condition, for example, a brain injury.

24 Claims, 5 Drawing Sheets

(56) References Cited

OTHER PUBLICATIONS

Pandya, Jignesh D. et al., N-acetylcysteineamide confers neuroprotection, improves bioenergetics and behavioral outcome following TBI, Jul. 2014, Exp Neurol. 257: 106-113.doi:10.1016/j.expneurol.2014.04.020.

Patel, Jignesh, Intranasal Route For Cns Delivery: Overview And Recent Advancements, 2017, European Journal of Pharmaceutical And Medical Research, 4(06), 281-292.

Product Information, Acetadote® Concentrated Injection, pp. 1-8, name and address of the sponsor Phebra Pty Ltd, date of most recent amendment Jan. 16, 2013.

Roth, Theodore L. et al., Transcranial Amelioration Of Inflammation And Cell Death Following Brain Injury, Nature, Jan. 9, 2014; 505(7482): 223-228. doi:10.1038/nature12808.

Rushworth, Gordon F. et al., Existing and potential therapeutic uses for N-acetylcysteine: The need for conversion to intracellular glutathione for antioxidant benefits, 2014, Pharmacology& Therapeutics 141, pp. 150-159.

Timmer, J.G. et al., Plasma Level Monitoring Of N-Acetylcysteine In Patients With Amyotrophic Lateral Sclerosis, 1984, Pharmaceutisch Weekblad Scientific Edition, vol. 6, p. 273.

Vavilala, Monica S et al., Change in blood-brain barrier permeability during pediatric diabetic ketoacidosis treatment, Pediatric critical care medicine : a journal of the Society of Critical Care Medicine and the World Federation of Pediatric Intensive and Critical Care Societies vol. 11,3 (2010): 332-8. doi:10.1097/PCC.0b013e3181c013f4.

Xiong, Y et al., Effect of N-Acetylcysteine on Mitochondrial Function Following Traumatic Brain Injury in Rats, 1999, Journal of Neurotrauma, vol. 16, No. 11, pp. 1067-1082.

Xiong, Ye et al., Animal models of traumatic brain injury, Nat Rev Neurosci, Feb. 2013; 14(2):128-142. doi:10.1038/nrn3407.

Xiong, Ye et al., Current understanding of neuroinflammation after traumatic brain injury and cell-based therapeutic opportunities, Chinese Journal of Traumatology 21 (2018) 137-151.

Zhou, Jie et al., Intravenous Administration of Stable-Labeled N-Acetylcysteine Demonstrates an Indirect Mechanism for Boosting Glutathione and Improving Redox Status, 2015, Journal of Pharmaceutical Sciences 104:2619-2626.

Bega, D. et al.; Clinical utility of DaTscan in patients with suspected Parkinsonian syndrome: a systematic review and meta-analysis; npj Parkinsons Disease 7, 43 (2021); published May 24, 2021; https://doi.org/10.1038/s41531-021-00185-8; 8 pages.

Sampedro, Frederic et al.; Dopaminergic degeneration induces early posterior cortical thinning in Parkinson's disease, Neurobiology of Disease, vol. 124, 2019; ISSN 0969-9961, https://doi.org/10.1016/j.nbd.2018.11.001; pp. 29-35 (7 pages).

Sampedro, Frederic et al.; Cortical macro and microstructural correlates of cognitive and neuropsychiatric symptoms in Parkinson's disease; Clinical Neurology and Neurosurgery, vol. 224, 2023, 107531; ISSN 0303-8467, https://doi.org/10.1016/j.clineuro.2022.107531; 8 pages.

GE Healthcare; Prescribing Information, DATSCAN (ioflupane I 123 injection), for intravenous use Initial U.S. Approval: 2011; 11 pages.

A.

B.

METHODS OF TREATING BRAIN DISORDERS

CROSS REFERENCE

This application claims the benefit of U.S. Provisional Application No. 62/970,254, filed Feb. 5, 2020, and U.S. Provisional Application No. 62/949,640, filed Dec. 18, 2019, each of which is hereby incorporated by reference in their entireties.

BACKGROUND

Concussions, also known as mild traumatic brain injuries (mTBIs), are transient and clinically detectable alterations in brain function resulting from mechanical insult transmitted to the brain. N-acetylcysteine (NAC) acts as an antioxidant, brain glutathione (GSH) precursor, and inhibitor of neuro-excitotoxicity and neuro-inflammation, and can be used to treat post-TBI neurotoxicity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

Disclosed herein is a method of treating a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, and wherein the subject is not substantially systemically exposed to the NAC, or the congener thereof, upon the intranasal administration.

Disclosed herein is a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC, or the congener thereof, to the brain from the nose, wherein substantially all of the NAC, or the congener thereof, enters the brain without crossing a blood brain barrier of the subject.

Disclosed herein is a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

Disclosed herein is a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC, or the congener thereof, to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

Disclosed herein is a method of treating a brain disorder in a brain of a subject in need thereof, the method comprising intranasally administering to a nose of the subject N-acetylcysteine NAC, or a congener thereof, wherein the intranasal administration provides a therapeutically-effective amount of the NAC, or the congener thereof, to the brain from the nose, wherein the NAC, or the congener thereof, crosses a respiratory epithelium of the subject after the intranasal administration, and then after crossing the respiratory epithelium, the NAC crosses a trigeminal nerve of the subject, and then after crossing the trigeminal nerve, then NAC enters the brain.

Further disclosed herein is a method of treating a brain disorder in a brain of a subject in need thereof, the method comprising intranasally administering to the nose of the subject N-acetylcysteine NAC, or a congener thereof, wherein the intranasal administration provides a therapeutically-effective amount of the NAC, or the congener thereof, to the brain from the nose, wherein the NAC, or the congener thereof, crosses a respiratory or olfactory epithelium, the NAC traverses the nasal rostral migratory stream pathway, and then after traversing the rostral migratory stream pathway, enters the brain.

BRIEF DESCRIPTION OF THE DRAWINGS

FIG. 1 PANEL B illustrates nose-to-brain pathways of drug delivery and a nose-to-blood-to-brain pathway traversing the systemic circulation and the blood brain barrier.

DETAILED DESCRIPTION

Figure 1:
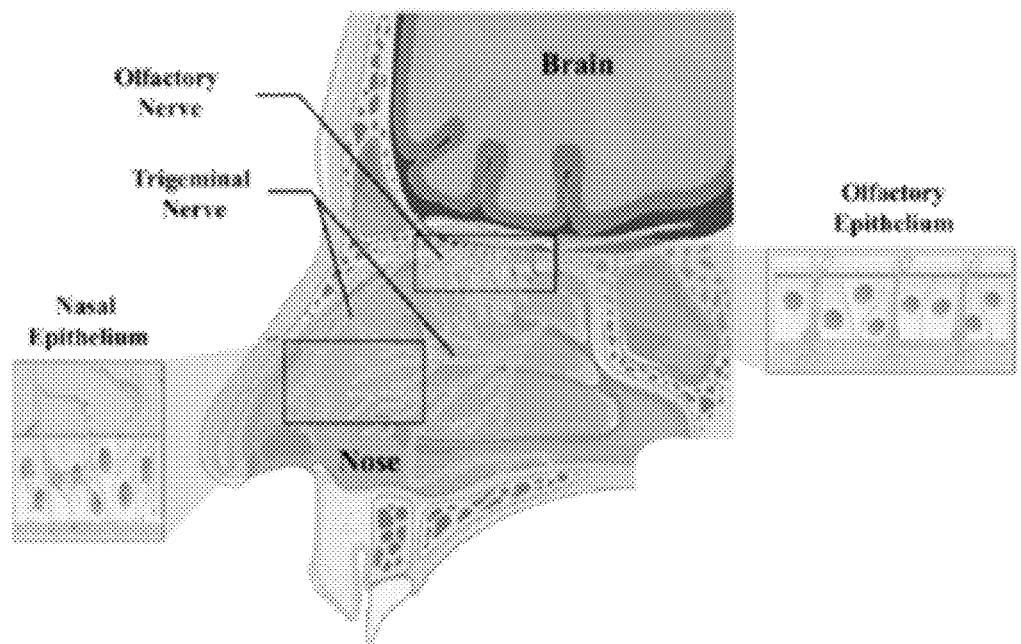
FIG. 1 PANEL A illustrates nasal innervation.
Figure 1:
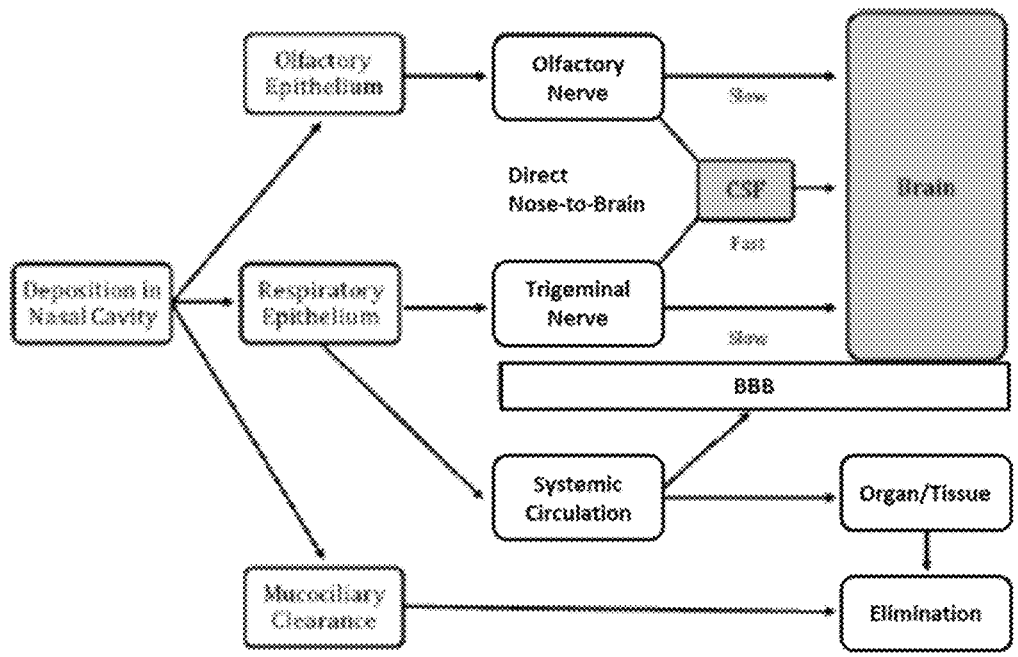

Concussions, also known as mild traumatic brain injuries (mTBIs), are transient and clinically detectable alterations in brain function resulting from mechanical insult transmitted to the brain. N-acetylcysteine NAC acts as an antioxidant, brain glutathione (GSH) precursor, and inhibitor of neuro-excitotoxicity and neuro-inflammation, and can be used to treat post-TBI neurotoxicity.

NAC is a small molecule precursor of L-cysteine that results in glutathione elevation biosynthesis. NAC is a powerful antioxidant that acts directly as a scavenger of free radicals, for example, oxygen free radicals. NAC has a range of pleotropic salutary effects on acute and chronic central nervous system (CNS) disorders through a variety of biochemical and pharmacological mechanisms of action, including quenching of reactive oxygen species (ROS), chelation of oxidative reactive metal ions, anti-inflammation, and neuromodulation via the cystine-glutamate antiporter. NAC can also increase the concentration and bioavailability of the endogenous antioxidant glutathione (GSH), anti-excitotoxic activity, and heavy metal-chelating activity.

NAC, NAC congeners, and NAC derivatives can exhibit beneficial effects in acute and chronic, focal, and diffuse forms of brain injury and brain disorders, including traumatic brain injury (TBI) in humans and pre-clinical animal models. The pharmacological properties of NAC derive from NAC's metabolic conversion to cysteine and reduced GSH, which provide protection against damaging neuro-excitotoxicity, oxidative damage, and inflammation. NAC provides protection against neuro-excitotoxicity by generating cysteine, a substrate for the cysteine-glutamate transporter. However, NAC has poor systemic availability and poor oral bioavailability due to high first-pass hepatic metabolism and uncertain transfer across the blood-brain barrier (BBB). Tolerable dose-volumes of readily available aqueous solutions of NAC often cannot achieve sufficient levels of measured brain penetrability and/or bioactivity.

Provided herein are methods of administering NAC or GSH to the central nervous system (CNS) using intranasal (IN) nose-to-brain direct delivery.

In some embodiments, the disclosure provides a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC, or the congener thereof, to the brain from the nose, and wherein the subject is not substantially systemically exposed to the NAC, or the congener thereof, upon the intranasal administration. In some embodiments, the disclosure provides a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC, or the congener thereof, to the brain from the nose, wherein substantially all of the NAC, or the congener thereof, enters the brain without crossing a blood brain barrier of the subject.

In some embodiments, the disclosure provides a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain. In some embodiments, the disclosure provides a method of treating a brain disorder in a brain of a subject in need thereof, the method comprising intranasally administering to a nose of the subject a dose of N-acetylcysteine NAC, or a congener thereof, wherein the intranasal administration provides a therapeutically-effective amount of the NAC, or the congener thereof, to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

In some embodiments, the disclosure provides a method of treating a brain disorder in a brain of a subject in need thereof, the method comprising intranasally administering to a nose of the subject N-acetylcysteine NAC, or a congener thereof, wherein the intranasal administration provides a therapeutically-effective amount of the NAC, or the congener thereof, to the brain from the nose, wherein the NAC, or the congener thereof, crosses a respiratory epithelium of the subject after the intranasal administration, and then after crossing the respiratory epithelium, the NAC crosses a trigeminal nerve of the subject, and then after crossing the trigeminal nerve, then NAC enters the brain.

Compounds of the Disclosure

NAC is a glutathione prodrug that is used to treat acetaminophen-induced liver failure and to loosen thick mucus individuals with cystic fibrosis or chronic obstructive pulmonary disease. NAC can be taken intravenously, by mouth, or inhaled as a mist. Common side effects of NAC include nausea and vomiting when NAC is administered orally. NAC can also cause skin redness and itching and a non-immune type of anaphylaxis. NAC has multiple putative targets of action, and NAC has poor penetration into the CNS. NAC has been reported to cause nausea and vomiting, induce bronchospasm, slow blood clotting, and induce neurotoxicity in a dose-dependent manner. These issues can be problematic for patients with hemorrhagic stroke.

The present disclosure describes the use of at least one compound or a pharmaceutically-acceptable salt thereof to treat a condition. In some embodiments, the compound is N-acetylcysteine NAC, NAC amide (NACA), NAC derivative, NAC metabolite, NAC congener, or NAC dendrimer (D-NAC), or a pharmaceutically-acceptable salt thereof. In some embodiments, the compound is a NAC prodrug or a pharmaceutically-acceptable slat thereof. In some embodiments, the compounds is NAC. In some embodiments, the compound is a NAC derivative. In some embodiments, the NAC derivative is GSH.

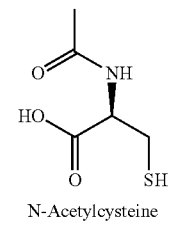

N-Acetylcysteine

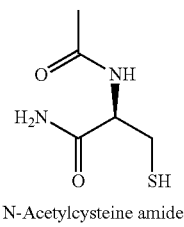

N-Acetylcysteine amide

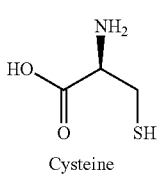
Cysteine

In some embodiments, the compound is a NAC dendrimer. Dendrimer-NAC (D-NAC) is a dendrimer conjugate where NAC is covalently bound to the surface of a dendrimer by disulfide linkages. In some embodiments, D-NAC comprises a polyamidoamine (PAMAM) hydroxyl dendrimer. In some embodiments, D-NAC comprises a polyglycerol sulfate dendrimer. In some embodiments, D-NAC comprises a polyamine dendrimer. In some embodiments, D-NAC comprises a polyamide dendrimer. In some embodiments, D-NAC comprises a linker. In some embodiments, GABA comprises a gamma-aminobutyric acid (GABA) linker. In some embodiments, D-NAC comprises a succinimidyl 3-(2-pyridyldithio)propionate (SPDP) linker.

In some embodiments, D-NAC has the formula:

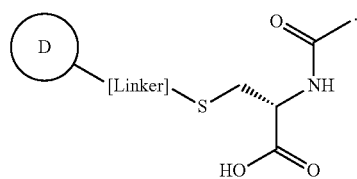

In some embodiments, D-NAC has the formula:

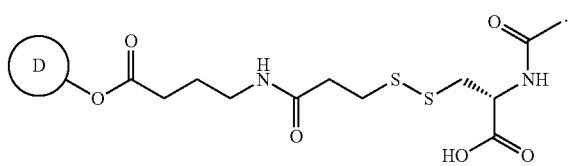

Purity of Compounds of the Disclosure

Any compound of the disclosure (e.g., NAC, a NAC congener, or a NAC derivative) can be purified. A compound of the disclosure (e.g., NAC, a NAC congener, or a NAC derivative) can be designated a drug. A compound as described herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Intranasal Nose-to-Brain Delivery

As demonstrated herein, the nasal cavity is suitable for drug delivery as the nasal mucosa provides for efficient absorption of pharmaceutically active molecules. The roof of the nasal cavity is located in close vicinity to the brain and harbors nerves that project to the brain. Therefore, a useful strategy to bypass the blood-brain barrier is the delivery of drugs from the nose to the brain (referred to herein as "nose-to-brain" or "N2B"). The nose-to-brain drug administration route delivers substances to the brain via the olfactory and/or trigeminal nerve. Nose-to-brain delivery can be used to deliver small molecule drugs, peptides or proteins, stem cells, viruses, and nucleotides.

Thus, pharmaceutically active small molecules (e.g., NAC or GSH) or biologic molecules (e.g., peptides) deposited on the nasal mucosa can traverse directly to the CNS by one or more multiple alternative or complementary pathways. The effectiveness of CNS delivery can depend on the anatomical site of deposition, molecular characteristics of the drug or biologic, the formulation, and the animal species under consideration. Nose-to-brain delivery can be minimally invasive with adequate patient compliance.

Disclosed herein is the use of intranasal administration of NAC, NACA, NAC derivative, NAC metabolite, NAC congener, or D-NAC to optimize nose-to-brain delivery of a compound of the disclosure to one or more regions of the brain that are susceptible to, or have undergone, injury from an acute or chronic brain disorder. In some embodiments, intranasal nose-to-brain delivery of NAC, NACA, NAC derivative, NAC metabolite, NAC congener, or D-NAC can prevent, lessen the likelihood of developing, delay, or ameliorate a brain injury. In some embodiments, intranasal nose-to-brain delivery of NAC, NACA, NAC derivative, NAC metabolite, NAC congener, or D-NAC can improve or prevent signs, symptoms, or disabilities associated with brain injury. In some embodiments, intranasal nose-to-brain delivery of NAC, NACA, NAC derivative, NAC metabolite, NAC congener, or D-NAC can improve or prevent signs or symptoms of treatment-resistant depression. In some embodiments, the NAC congener is GSH.

Also disclosed herein are delivery devices and formulations that promote direct transfer of NAC, NACA, NAC derivative, NAC metabolite, NAC congener, or D-NAC to the brain while avoiding systemic circulation that eliminates the active substances, thereby avoiding systemic disposition. In some embodiments, the delivery devices and formulations of the disclosure promote direct transfer of NAC. In some embodiments, the delivery devices and formulations of the disclosure promote direct transfer of GSH. The intranasal NAC or GSH formulations of the disclosure are designed to facilitate entry of NAC, NACA, NAC derivative, NAC metabolite, NAC congener, or D-NAC into specific portals for anatomical pathways of nose-to-brain drug transfer. In some embodiments, the intranasal NAC or GSH formulations of the disclosure maximizes entry of NAC, NACA, NAC derivative, NAC metabolite, NAC congener, or D-NAC via nose-to-brain drug transfer by allowing higher concentrations of NAC or GSH to be delivered to the nasal mucosal surface. In some embodiments, the intranasal NAC or GSH formulations of the disclosure maximizes entry of NAC, NACA, NAC derivative, NAC metabolite, NAC congener (e.g., GSH), or D-NAC via nose-to-brain drug transfer by minimizing local loss of nasally delivered NAC or GSH by mucociliary clearance and elimination via systemic circulation. In some embodiments, the intranasal NAC or GSH formulations of the disclosure maximizes entry of NAC, NACA, NAC derivative, NAC metabolite, NAC congener (e.g., GSH), or D-NAC via nose-to-brain drug transfer by increasing delivery through the mucus barrier that coats the interior of the nasal cavity, and the delivery mechanism benefits from NAC's and GSH's intrinsic mucolytic characteristics. In some embodiments, the intranasal NAC or GSH formulations of the disclosure maximize entry of NAC, NACA, NAC derivative, NAC metabolite, NAC congener (e.g., GSH), or D-NAC via nose-to-brain drug transfer by enhancing transport through or between nasal epithelial cells or increasing uptake into the space surrounding nerve cells that project into the brain.

FIG. 1A illustrates nasal innervation. FIG. 1B illustrates nose-to-brain pathways of compound delivery and a nose-to-blood-to-brain pathway traversing the systemic circulation and the blood brain barrier. In some embodiments shown in FIG. 1B, nose-to-brain delivery is mediated via the olfactory pathway. In some embodiments, a compound disclosed herein (e.g., NAC, NACA, NAC derivative, NAC metabolite, NAC congener, or D-NAC) is administered in the nasal cavity, then crosses the olfactory epithelium, then after crossing the olfactory epithelium, the compound crosses the olfactory nerve, and then after crossing the olfactory nerve, the compound enters the brain. In some embodiments, a compound disclosed herein (e.g., NAC, NACA, NAC derivative, NAC metabolite, NAC congener, or D-NAC) is administered in the nasal cavity, then crosses the olfactory epithelium; then after crossing the olfactory epithelium, the compound crosses the olfactory nerve; then after crossing the olfactory nerve, the compound enters the cerebral spinal fluid; then after entering the cerebral spinal fluid, the compound enters the brain. In some embodiments, a compound (e.g., NAC, NACA, NAC derivative, NAC metabolite, NAC congener, or D-NAC) is administered in the nasal cavity, then crosses the olfactory epithelium, then after crossing the olfactory epithelium, the compound crosses the olfactory nerve, then after crossing the olfactory nerve, the compound directly enters the brain without passing through the cerebral spinal fluid.

In some embodiments shown in FIG. 1B, nose-to-brain delivery is mediated via the trigeminal pathway. In some embodiments, a compound disclosed herein (e.g., NAC, NACA, NAC derivative, NAC metabolite, NAC congener, or D-NAC) is administered in the nasal cavity, then crosses the respiratory epithelium; then after crossing the respiratory epithelium, the compound crosses the trigeminal nerve; and then after crossing the trigeminal nerve, the compound enters the brain. In some embodiments, a compound disclosed herein (e.g., NAC, NACA, NAC derivative, NAC metabolite, NAC congener, or D-NAC) is administered in the nasal cavity, then crosses the respiratory epithelium; then after crossing them respiratory epithelium, the compound crosses the trigeminal nerve; then after crossing the trigeminal nerve, the compound enters the cerebral spinal fluid; then after entering the cerebral spinal fluid, the compound enters the brain. In some embodiments, a compound disclosed herein (e.g., NAC, NACA, NAC derivative, NAC metabolite, NAC congener, or D-NAC) is administered in the nasal cavity, then crosses the respiratory epithelium; then after crossing the respiratory epithelium, the compound crosses the trigeminal nerve; then after crossing the trigeminal nerve, the compound directly enters the brain without passing through the cerebral spinal fluid.

Figure 2:
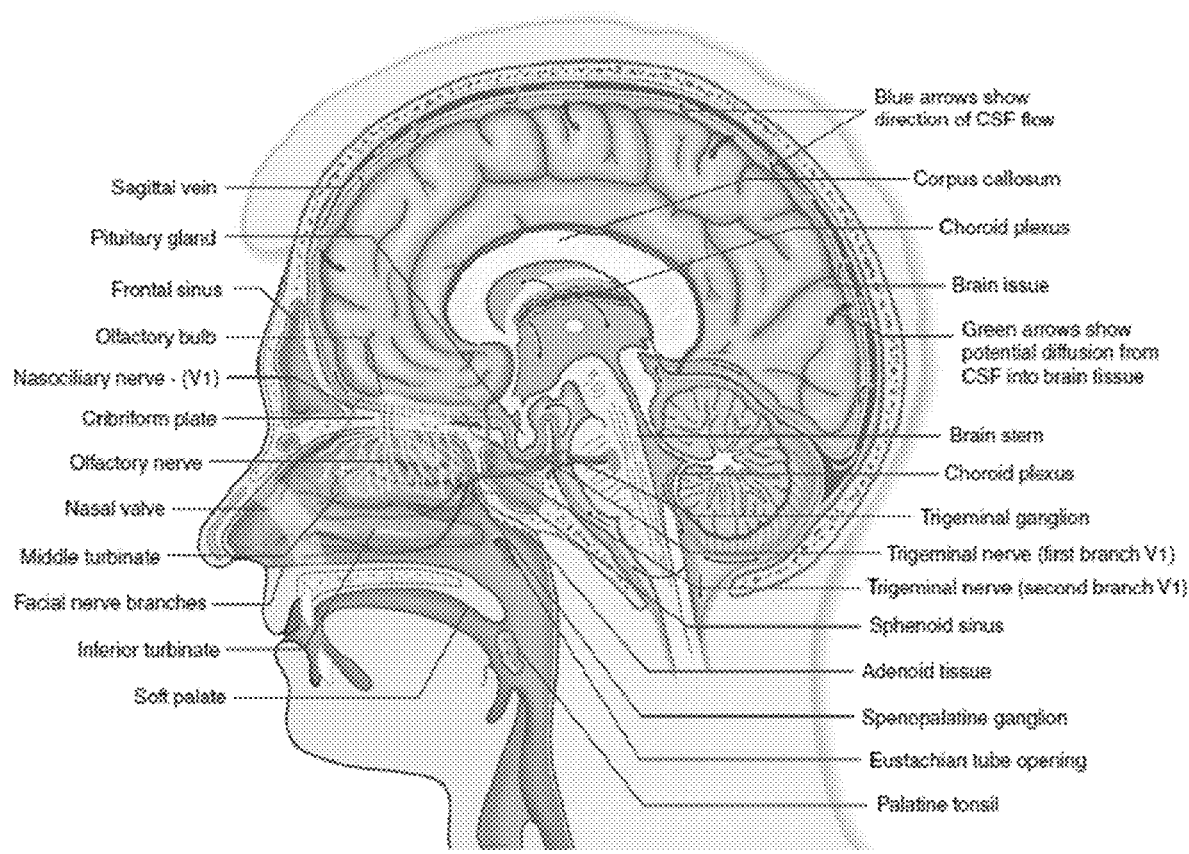
FIG. 2 illustrates a lateral section of the human nose and brain showing key anatomical structures and nerves relevant to drug transport from nose directly to the brain.
Figure 3:
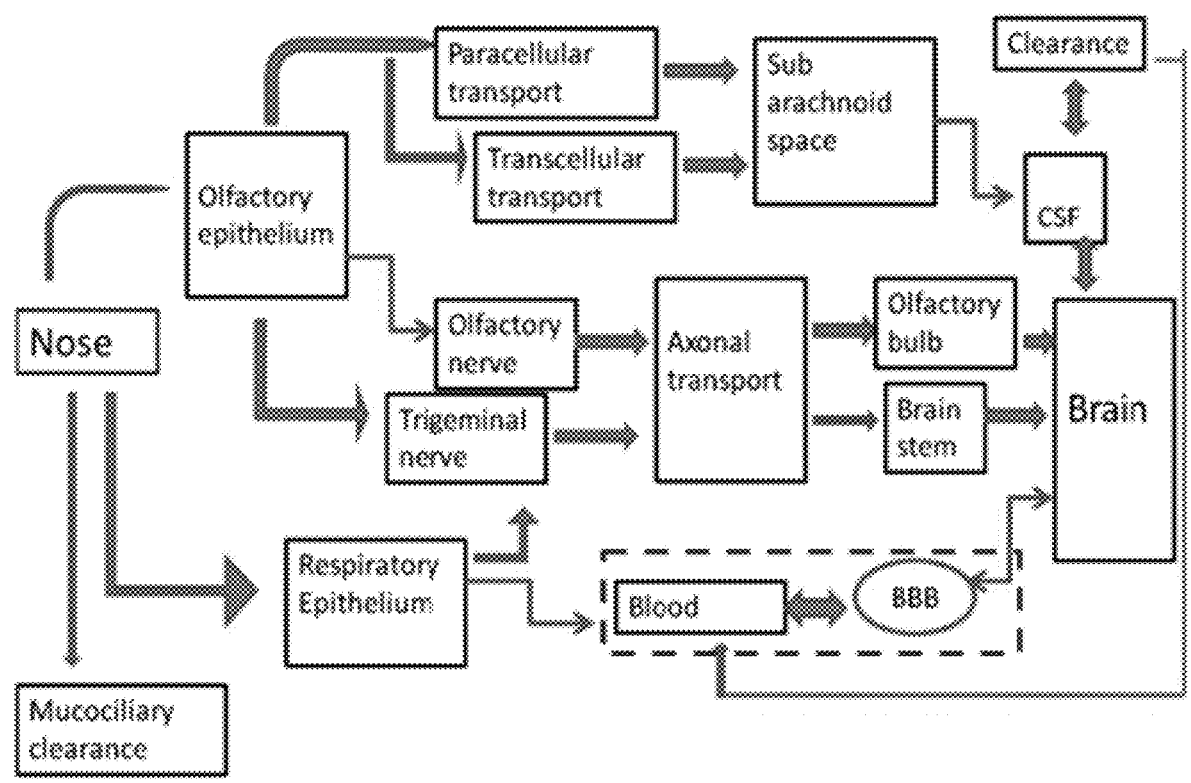
FIG. 3 illustrates different pathways after nasal administration of a drug disclosed herein.

FIG. 2 illustrates a lateral section of the human nose and brain showing key anatomical structures and nerves relevant to compound transport from the nose directly to the brain. FIG. 3 illustrates three different pathways after nasal administration of a compound disclosed herein. The multiple nasal surfaces, transport processes, and anatomical compartments through which a compound reaches the brain by non-blood-borne routes are shown. Nose-to-brain delivery of compounds avoids and is distinct from blood-borne routes of delivery that cross the blood-brain barrier (FIG. 3, shown in a dashed box). In some embodiments shown in FIG. 3, nose-to-brain delivery is mediated via the olfactory pathway. In some embodiments, a compound disclosed herein (e.g., NAC, NACA, NAC derivative, NAC metabolite, NAC congener, or D-NAC) is administered in the nasal cavity, then crosses the olfactory epithelium; then after crossing the olfactory epithelium, the compound crosses the subarachnoid space. A compound disclosed herein can enter the subarachnoid space through paracellular transport. Additionally or alternatively, a compound can enter the subarachnoid space through transcellular transport. Then, after entering the subarachnoid space, the compound enters the cerebral spinal fluid; then after entering the cerebral spinal fluid, the compound enters the brain. In some embodiments shown in FIG. 3, a compound disclosed herein (e.g., NAC, NACA, NAC derivative, NAC metabolite, NAC congener, or D-NAC) is administered in the nasal cavity, then crosses the olfactory epithelium; then after crossing the olfactory epithelium, the compound crosses the olfactory nerve; then after crossing the olfactory nerve, the compound enters the olfactory bulb through an axonal transport mechanism. Then, after entering the olfactory bulb, the compound enters the brain. In some embodiments shown in FIG. 3, a compound disclosed herein (e.g., NAC, NACA, NAC derivative, NAC metabolite, NAC congener, or D-NAC) is administered in the nasal cavity, then crosses the olfactory epithelium, then after crossing the olfactory epithelium, the compound crosses the olfactory nerve; then after crossing the olfactory nerve, the compound enters the brain stem through an axonal transport mechanism. Then, after entering the brain stem, the compound enters the brain.

In some embodiments shown in FIG. 3, nose-to-brain delivery is mediated via the trigeminal pathway. In some embodiments, a compound disclosed herein (e.g., NAC, NACA, NAC derivative, NAC metabolite, NAC congener, or D-NAC) is administered in the nasal cavity, then crosses the olfactory epithelium; then after crossing the olfactory epithelium, the compound crosses the trigeminal nerve; then after crossing the trigeminal nerve, the compound enters the olfactory bulb through an axonal transport mechanism. Then, after entering the olfactory bulb, the compound enters the brain. In some embodiments shown in FIG. 3, a compound disclosed herein (e.g., NAC, NACA, NAC derivative, NAC metabolite, NAC congener, or D-NAC) is administered in the nasal cavity, then crosses the olfactory epithelium; then after crossing the olfactory epithelium, the compound crosses the trigeminal nerve; then after crossing the trigeminal nerve, the compound enters the brain stem through an axonal transport mechanism. Then, after entering the brain stem, the compound enters the brain. In some embodiments shown in FIG. 3, a compound disclosed herein (e.g., NAC, NACA, NAC derivative, NAC metabolite, NAC congener, or D-NAC) is administered in the nasal cavity, then crosses the respiratory epithelium; then after crossing the respiratory epithelium, the compound crosses the trigeminal nerve; then after crossing the trigeminal nerve, the compound enters the olfactory bulb through an axonal transport mechanism. Then, after entering the olfactory bulb, the compound enters the brain. In some embodiments shown in FIG. 3, a compound of the disclosure is administered in the nasal cavity, then crosses the respiratory epithelium; then after crossing the respiratory epithelium, the compound crosses the trigeminal nerve; then after crossing the trigeminal nerve, the compound enters the brain stem through an axonal transport mechanism. Then, after entering the brain stem, the compound enters the brain.

Figure 4:
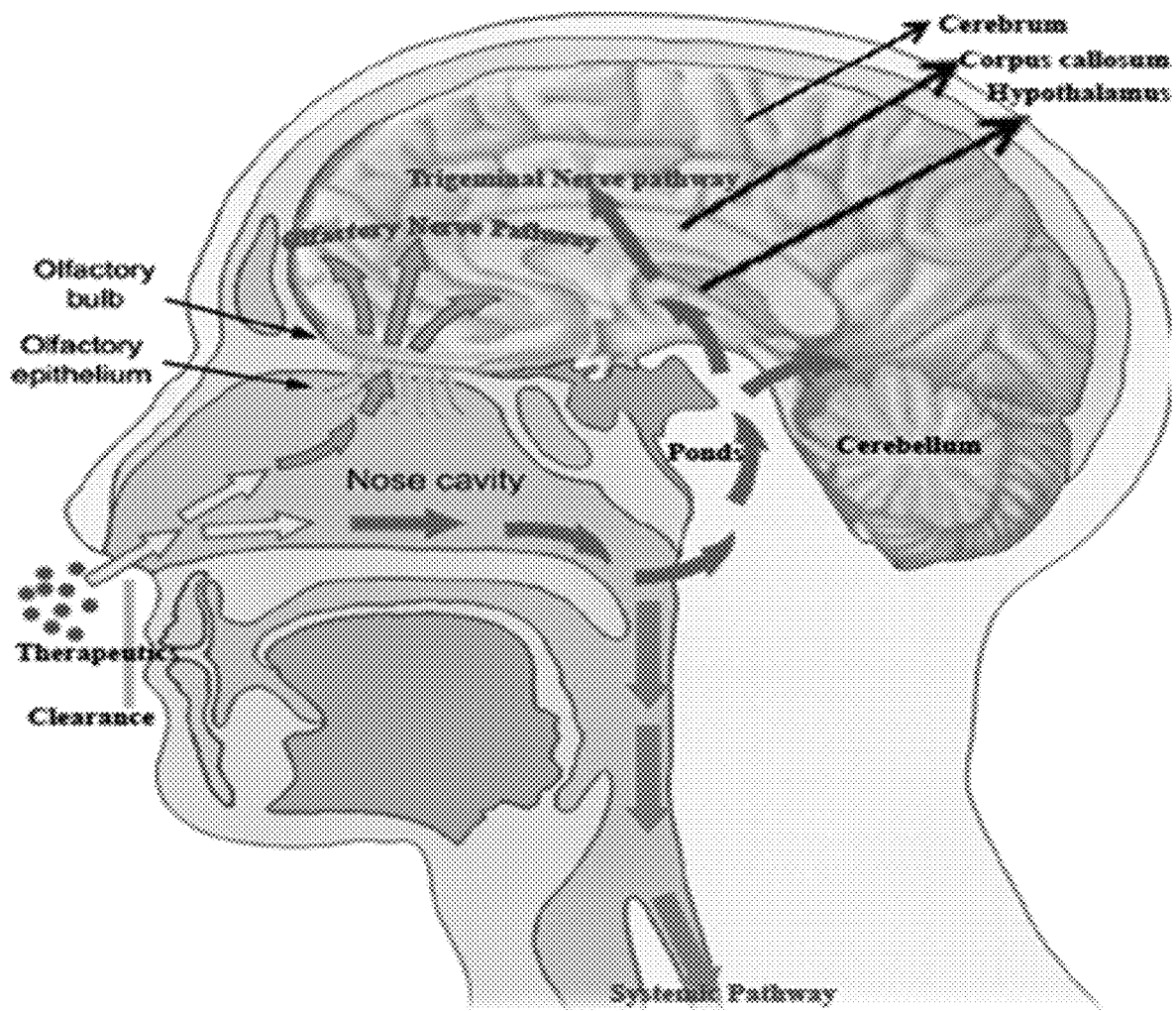
FIG. 4 illustrates a different direct nose-to-brain transport mechanism of a therapeutic disclosed herein.

FIG. 4 illustrates a different direct nose-to-brain transport mechanism of therapeutics, which can result in different distributions of the therapeutic to different regions of the brain.

Nose-to-brain portals of direct targeted entry into the CNS in various species include: 1) localized perivascular flow along lymphatic, venous, and arterial vessels, and across local intravascular counter-current arterio-venous anastomoses; 2) neuronal and perineuronal transport along the cranial nerves; 3) transport through the cribriform plate along post-embryologically persistent rostral migratory stream; and 4) flow through the cerebrospinal fluid (CSF) and/or choroid plexus. The nose-to-brain pathways bypass systemic circulation, circumvent elements of the blood-brain barrier, and selectively delivers compounds to specific regions or sub-structures within the brain. Specific regions and sub-structures within the brain can be selectively involved in different types of brain disorders, such as mTBI (i.e., concussion) or Parkinson's Disease.

In some embodiments, after administration, a compound of the disclosure can be transported through the olfactory pathway. In some embodiments, after administration, a compound of the disclosure can be transported through the trigeminal pathway. In some embodiments, the compound of the disclosure does not pass through the blood brain barrier. In some embodiments, the subject receiving the compound is not substantially systemically exposed to the compound. In some embodiments, a portion of the compound can be transported through the olfactory pathway, and another portion of the compound can be transported through the trigeminal pathway. In some embodiments, about 1% to about 99% of the compound can be transported through the olfactory pathway, and about 99% to about 1% of the compound can be transported through the trigeminal pathway. In some embodiments, about 5% to about 95% of the compound can be transported through the olfactory pathway, and about 95% to about 5% of the compound can be transported through the trigeminal pathway. In some embodiments, about 10% to about 90% of the compound can be transported through the olfactory pathway, and about 90% to about 10% of the compound can be transported through the trigeminal pathway. In some embodiments, about 15% to about 85% of the compound can be transported through the olfactory pathway, and about 85% to about 15% of the compound can be transported through the trigeminal pathway. In some embodiments, about 20% to about 80% of the compound can be transported through the olfactory pathway, and about 80% to about 20% of the compound can be transported through the trigeminal pathway. In some embodiments, about 25% to about 75% of the compound can be transported through the olfactory pathway, and about 75% to about 25% of the compound can be transported through the trigeminal pathway. In some embodiments, about 30% to about 70% of the compound can be transported through the olfactory pathway, and about 70% to about 30% of the compound can be transported through the trigeminal pathway. In some embodiments, about 35% to about 65% of the compound can be transported through the olfactory pathway, and about 65% to about 35% of the compound can be transported through the trigeminal pathway. In some embodiments, about 40% to about 60% of the compound can be transported through the olfactory pathway, and about 60% to about 40% of the compound can be transported through the trigeminal pathway. In some embodiments, about 55% to about 45% of the compound can be transported through the olfactory pathway, and about 45% to about 55% of the compound can be transported through the trigeminal pathway. In some embodiments, about 50% of the compound can be transported through the olfactory pathway, and about 50% of the compound can be transported through the trigeminal pathway.

In some embodiments, a compound can be transported through olfactory pathway and trigeminal pathway at an olfactory: trigeminal ratio of about 1:99, about 2:98, about 3:97, about 4:96, about 5:95, about 6:94, about 7:93, about 8:92, about 9:91, about 10:90, about 11:89, about 12:88, about 13:87, about 14:86, about 15:85, about 16:84, about 17:83, about 18:82, about 19:81, about 20:80, about 21:79, about 22:78, about 23:77, about 24:76, about 25:75, about 26:74, about 27:73, about 28:72, about 29:71, about 30:70, about 31:69, about 32:68, about 33:67, about 34:66, about 35:65, about 36:64, about 37:63, about 38:62, about 39:61, about 40:60, about 41:59, about 42:58, about 43:57, about 44:56, about 45:55, about 46:54, about 47:53, about 48:52, about 49:51, about 50:50, about 51:49, about 52:48, about 53:47, about 54:46, about 55:45, about 56:44, about 57:43, about 58:42, about 59:41, about 60:40, about 61:39, about 62:38, about 63:37, about 64:36, about 65:35, about 66:34, about 67:33, about 68:32, about 69:31, about 70:30, about 71:29, about 72:28, about 73:27, about 74:26, about 75:25, about 76:24, about 77:23, about 78:22, about 69:21, about 80:20, about 81:19, about 82:18, about 83:17, about 84:16, about 85:15, about 86:14, about 87:13, about 88:12, about 89:11, about 90:10, about 91:9, about 92:8, about 93:7, about 94:6, about 95:5, about 96:4, about 97:3, about 98:2, or about 99:1.

In some embodiments, a compound of the disclosure (e.g., NAC, NACA, NAC derivative, NAC metabolite, NAC congener, or D-NAC) does not enter the systemic circulation. Thus, in some embodiments, the subject is not substantially systemically exposed to the compound of the disclosure. In some embodiments, the compound of the disclosure does not cross the blood brain barrier. In some embodiments, a compound of the disclosure is administered in the nasal cavity, then crosses the respiratory epithelium; then after crossing the respiratory epithelium, the compound crosses the trigeminal nerve without entering the systemic circulation; then after crossing the trigeminal nerve, the compound enters the brain without entering the systemic circulation or crossing the blood-brain barrier.

In some embodiments, although the subject is not substantially systemically exposed to a compound of the disclosure, a portion of administered amount of the compound can enter systemic circulation. In some embodiments, a dose of a compound entering the respiratory epithelium partially enters the systemic circulation. In some embodiments, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20% or more enters the systemic circulation. In some embodiments, less than about 50% of the compound enters the systemic circulation. In some embodiments, less than about 40% of the compound enters the systemic circulation. In some embodiments, less than about 30% of the compound enters the systemic circulation. In some embodiments, less than about 20% of the compound enters the systemic circulation. In some embodiments, less than about 10% of the compound enters the systemic circulation. In some embodiments, less than about 5% of the compound enters the systemic circulation. In some embodiments, less than about 1% of the compound enters the systemic circulation.

In some embodiments, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19% or about 20% or more crosses the blood brain barrier. In some embodiments, less than about 50% of the compound crosses the blood brain barrier. In some embodiments, less than about 40% of the compound crosses the blood brain barrier. In some embodiments, less than about 30% of the compound crosses the blood brain barrier. In some embodiments, less than about 20% of the compound crosses the blood brain barrier. In some embodiments, less than about 10% of the compound crosses the blood brain barrier. In some embodiments, less than about 5% of the compound crosses the blood brain barrier. In some embodiments, less than about 1% of the compound crosses the blood brain barrier.

Therapeutic Methods

The present disclosure describes the use of a compound and methods to treat a brain disorder. The disclosure also describes techniques to target NAC, NACA, NAC derivative, NAC metabolite, NAC congener, or D-NAC directly to the CNS while avoiding high first-pass hepatic metabolism and circumventing the blood brain barrier. In some embodiments, the compounds and methods of the disclosure e can be used to treat a brain disorder. In some embodiments, the compounds and methods of the disclosure can be used to treat a brain injury. In some embodiments, the brain disorder can be a form of brain damage, for example, brain damage resulting from a traumatic brain injury. In some embodiments, the brain disorder can be a disorder of the nervous system. Structural, biochemical, or electrical abnormalities in the brain, spinal cord, or other nerves can result in a range of symptoms. Examples of symptoms that arise from neurological disorders include paralysis, muscle weakness, poor coordination, loss of sensation, seizures, confusion, pain, and altered levels of consciousness.

The compounds and methods of the disclosure can be used to treat a CNS condition. CNS disorders are a group of neurological disorders that affect the structure or function of the brain or spinal cord, which collectively form the CNS. The disclosure describes compounds and methods to treat a CNS disorder caused by traumatic brain injury, mild traumatic brain injury, concussion, mild concussion, post-concussion syndrome, infections, degeneration (e.g., degenerative spinal disorders), structural defects (e.g., anencephaly, hypospadias, spina bifida, microgyria, polymicrogyria, bilateral frontoparietal polymicrogyria, or pachgyria), tumors, autoimmune disorders, or stroke. In some embodiments, the disclosure describes compounds and methods of treating the use of a compound of the disclosure to treat traumatic brain injury. In some embodiments, the disclosure describes the use of a compound of the disclosure to treat mild traumatic brain injury. In some embodiments, the disclosure describes the use of a compound of the disclosure to treat subarachnoid hemorrhage. In some embodiments, the disclosure describes the use of a compound of the disclosure to treat concussion. In some embodiments, the disclosure describes the use of a compound of the disclosure to treat a mild concussion. In some embodiments, the disclosure describes the use of a compound of the disclosure to treat post-concussion syndrome.

In some embodiments, the disclosure describes the use of a compound of the disclosure to treat stroke. Stroke is a medical condition in which poor blood flow to the brain results in cell death. The two main types of strokes are ischemic stroke resulting from a lack of blood flow, and hemorrhagic stroke resulting from bleeding. Signs and symptoms of a stroke include an inability to move or feel on one side of the body, problems understanding or speaking, and a loss of vision to one side. In some embodiments, the disclosure describes the use of a compound of the disclosure to treat hemorrhagic stroke. In some embodiments, the disclosure describes the use of a compound of the disclosure to treat ICH stroke.

In some embodiments, the present disclosure describes the use of a compound of the disclosure for treating brain damage. In some embodiments, the brain damage is due to brain injury resulting from an acute event, such as traumatic brain injury. Brain injury resulting from an acute event is sometimes referred to as primary brain injury. In some embodiments, the disclosure describes the use of a compound of the disclosure to treat traumatic brain injury. In some embodiments, the disclosure describes the use of a compound of the disclosure to treat mild traumatic brain injury. Brain injury resulting from an acute event can be caused by a blow to the head from, e.g., falls, violence, accidents, child abuse, sports injuries, and blast injuries due to explosions. In some embodiments, the present disclosure describes the use of a compound of the disclosure for treating a concussion. In some embodiments, the present disclosure describes the use of a compound of the disclosure for treating a mild concussion.

In some embodiments, a compound of the disclosure is used to treat brain damage due to subsequent secondary brain injury resulting from primary brain injury. A secondary brain injury can include the changes that evolve over a period of hours to days after the primary brain injury. Secondary brain injury includes a cascade of cellular, chemical, tissue, or blood vessel changes in the brain that contribute to further destruction of brain tissue.

In some embodiments, a compound of the disclosure is used to treat a brain injury resulting from exposure to agents that are involved in secondary brain damage or neurodegeneration, such as glutamate, glutamate receptor ligands, hypoxia-mimicking agents, nitric oxide generating agents, apoptosis-inducing agents, steroids, ammonium chloride, toxic compounds, or agents that interfere with ATP production. In some embodiments, a compound of the disclosure is used to treat brain damage due to a chronic challenge such as infection, toxins, and excessive drug use of recreational, over the counter, and/or prescription drugs.

In some embodiments, the compounds and methods of the present disclosure can be used to treat military personnel, for example, soldiers in the battlefield, especially soldiers who have suffered traumatic brain injury and/or secondary brain damage resulting from traumatic brain injury. In some embodiments, the compounds and methods of the disclosure can be used to treat traumatic brain injury and/or secondary brain damage resulting from traumatic brain injury can be treated by administering the compounds of the disclosure to soldiers, for example by supplying the compounds of the disclosure to paramedics and/or the soldiers in the battlefield or under threat/at the site of terrorist attack, so that the compounds can be administered on site as soon as possible after a soldier experiences traumatic brain injury. The compounds and methods of the present disclosure can also be used to treat civilians who are victims of violent crimes, including but not limited to, terrorist attacks, and any other mishap that can cause brain damage. Treatment the compositions of the disclosure can reduce the incidence of disability presently occurring in the aftermath of traumatic brain injury suffered due to hostilities, including terrorist attacks, other crimes, and accidents.

In some embodiments, compounds of the disclosure can also be used to treat individuals suffering from brain injury due to domestic occurrences, such as traffic accidents (e.g., motor and non-motor vehicle accidents), sports injuries, work related accidents, household accidents, child abuse, domestic violence, and gunshot wounds, including consequential injuries such as disability or epilepsy. In some embodiments, the compounds are given prophylactically for contact sports having high incidence of CNS damage.

In some embodiments, the disclosure describes the use of a compound to treat brain damage in a specific region of the brain, such as cerebral lobe (e.g., basal ganglia, cerebellum, or the brainstem) damage, frontal lobe damage, parietal lobe damage, temporal lobe damage, or occipital lobe damage. In some embodiments, the present disclosure describes the use of a compound to treat brain dysfunction according to type: aphasia (language), dysgraphia (writing), dysarthria (speech), apraxia (patterns of sequences of movements), agnosia (identifying things or people), or amnesia (memory). In some embodiments the present disclosure describes the use of a compound to treat spinal cord disorders, peripheral neuropathy and other peripheral nervous system disorders, cranial nerve disorders (e.g., Trigeminal neuralgia), autonomic nervous system disorders (e.g., dysautonomia, Multiple System Atrophy), or seizure disorders (i.e., epilepsy).

In some embodiments, the disclosure describes the use of a compound to treat a movement disorder of the central and peripheral nervous system, such as Essential tremor, Amyotrophic lateral sclerosis, Tourette's syndrome, Multiple Sclerosis, and various types of peripheral neuropathy. In some embodiments, the disclosure describes the use of a compound to treat sleep disorders (e.g., narcolepsy), migraines and other types of headaches, or central neuropathy. In some embodiments, the disclosure describes the use of a compound to treat a neuropsychiatric illness, such as attention deficit hyperactivity disorder, autism, or obsessive compulsive disorder.

In some embodiments, the disclosure describes the use of a compound to treat a neurodegenerative disease. Generally, diseases of the central nervous system are referred to as neurodegenerative, and are characterized by gradually evolving, progressive neuronal death. In some embodiments, the neurodegenerative disease is hereditary with either dominant or recessive inheritance. In some embodiments, the neurodegenerative disease occurs sporadically. The compounds of the disclosure can treat brain damage, for example, brain damage resulting from a mechanical injury, disease, infections, toxic challenges, and excessive use of drugs including recreational, over the counter, or prescription drugs.

In some embodiments, the compounds of the disclosure and methods disclosed herein can be used to treat a neurodegenerative disease, for example, Alzheimer Disease, Parkinson Disease, Huntington Disease, Lou Gehrig Disease, Multiple Sclerosis, autoimmune disorders, Pick Disease, diffuse Lewy body Disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson-Dementia complex of Guam, subacute sclerosing panencephalitis, synucleinopathies, primary progressive aphasia, striatonigral degeneration, Machado-Joseph disease/spinocerebellar ataxia type 3 and olivopontocerebellar degenerations, Gilles De La Tourette Disease, bulbar and pseudobulbar palsy, spinal and spinobulbar muscular atrophy (Kennedy Disease), primary lateral sclerosis, familial spastic paraplegia, Werdnig-Hoffmann Disease, Kugelberg-Welander Disease, Tay-Sach Disease, Sandhoff Disease, familial spastic disease, Wohlfart-Kugelberg-Welander Disease, spastic paraparesis, progressive multifocal leukoencephalopathy, prion diseases, including Creutzfeldt-Jakob Disease, Gerstmann-Straussler-Scheinker Disease, Kuru, and fatal familial insomnia. In some embodiments, the neurological disease is Parkinson's Disease.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, and wherein the subject is not substantially systemically exposed to the NAC, or the congener thereof, upon the intranasal administration.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein substantially all of the NAC, or the congener thereof, enters the brain without crossing a blood brain barrier of the subject.

In some embodiments, the methods of the disclosure can treat a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

In some embodiments, the methods of the disclosure can treat a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

In some embodiments, the methods of the disclosure can treat a brain disorder in a brain of a subject in need thereof, the method comprising intranasally administering to a nose of the subject N-acetylcysteine (NAC), or a congener thereof, wherein the intranasal administration provides a therapeutically-effective amount of the NAC, or the congener thereof, to the brain from the nose, wherein the NAC, or the congener thereof, crosses a respiratory epithelium of the subject after the intranasal administration, and then after crossing the respiratory epithelium, the NAC crosses a trigeminal nerve of the subject, and then after crossing the trigeminal nerve, then NAC enters the brain.

In some embodiments, the methods of the disclosure can treat a brain disorder, wherein the brain disorder is a concussion. In some embodiments, the methods of the disclosure can treat a brain disorder, wherein the brain disorder is post-concussion syndrome. In some embodiments, the methods of the disclosure can treat a brain disorder, wherein the brain disorder is a mild traumatic brain injury. In some embodiments, the methods of the disclosure can treat a brain disorder, wherein the brain disorder is traumatic brain injury. In some embodiments, the methods of the disclosure can treat a brain disorder, wherein the brain disorder is associated with athletic activity. In some embodiments, the methods of the disclosure can treat a brain disorder, wherein the brain disorder is a neurodegenerative disease. In some embodiments, the methods of the disclosure can treat a brain disorder, wherein the brain disorder is dementia. In some embodiments, the methods of the disclosure can treat a brain disorder, wherein the brain disorder is age-related. In some embodiments, the methods of the disclosure can treat a brain disorder, wherein the brain disorder is Parkinson's disease. In some embodiments, the methods of the disclosure can treat a brain disorder, wherein the brain disorder is a stroke.

In some embodiments, the NAC congener is GSH. In some embodiments, substantially all of the dose enters the brain without crossing a blood brain barrier of the subject.

In some embodiments, the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain. In some embodiments, the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC enters the brain. In some embodiments, the NAC, or the congener thereof, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the brain.

In some embodiments, the therapeutically-effective amount is about 1 mg/kg to about 10 mg/kg. In some embodiments, the therapeutically-effective amount is from about 100 mg to about 400 mg. In some embodiments, the dose is administered using a nasal pump. In some embodiments, the dose is administered using an atomizer. In some embodiments, the dose is administered using a nebulizer. In some embodiments, substantially all of the dose enters a nasal cavity of the subject.

Pharmaceutical Compositions

The present disclosure describes pharmaceutical compositions comprising NAC, NACA, a NAC metabolite, NAC congener, or D-NAC, or a pharmaceutically-acceptable salt thereof that can be administered to a subject to treat brain injury or a CNS condition as described herein. A pharmaceutical composition of the disclosure can be a combination of any pharmaceutical compound described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. A pharmaceutical composition can be administered in a local manner, for example, via injection of the compound directly into an organ, optionally in a depot or sustained release formulation or implant.

A compound of the disclosure can be administered intranasally, and can be formulated into a variety of inhalable compositions, such as solutions, suspensions, vapors, or powders. Intranasal pharmaceutical compositions can contain solubilizers, stabilizers, tonicity enhancing agents, buffers and preservatives.

In practicing the methods of treatment or use provided herein, therapeutically-effective amounts of a compound described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compound used, and other factors. A compound of the disclosure can be used singly or in combination with one or more therapeutic agents as components of mixtures.

Pharmaceutical compositions of the disclosure can be formulated using one or more physiologically-acceptable carriers comprising excipients and auxiliaries, which facilitate processing of the active compounds into preparations that can be used pharmaceutically. A formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions of the disclosure can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising a compound described herein include formulating a compound with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in intranasal formulation of the disclosure include, but are not limited to, mucoadhesive excipients, adsorption enhancers, and preservatives, In some embodiments, the composition comprise mucoadhesive excipient. Mucoadhesive excipients include small molecules, oligomeric molecules or polymers. In some embodiments, mucoadhesive molecules are positively charged to build-up interactions with negatively charged mucins. The mucus consists predominantly of proteins of the mucin family and water. Mucins are bound to the apical surface of epithelial cells. By adhering to such cell bound mucins, these agents prolong the residence at the mucosa and, thus, improve drug uptake. Examples of mucoadhesive compounds include, but are not limited to, chitosan (a copolymer of N-acetyl-D-glucosamine and glucosamine), chitosan derivatives (e.g., N-trimethyl chitosan, carboxylated chitosan), Hypromellose (hydroxypropylmethyl cellulose), carbopol, carboxymethylcellulose, and polyacrylic acid.

In some embodiments, the composition comprise adsorption enhancers. Excipients that improve permeation and absorption are e.g., cyclodextrins, bile salts, laureth-9 sulfate, fusidate derivates, fatty acids, hydrophilic polymers, and surfactants. In some embodiments, methylated B-cyclodextrins are used to enhance the absorption of poorly water soluble, lipophilic drugs since they form inclusion complexes with the drug.

To prolong stability of nasal drug formulations, preservatives can be used. Non-limiting examples of preservatives include lipohilic preservatives such as chlorobutol, hydroxybenzoates, methylhydroxybenzoates, propylhxdroxybenzoates, chlorocresol, edetate, and benzalkonium chloride.

In some embodiments, the formulations are in solid or semi-sold forms, e.g., in the form of hydrogels. Examples of hydrogels include compositions comprising chitosan, carbopol, hydroxypropyl methylcellulose, and/or polyvinyl alcohol. Due to higher viscosity, semisolid formulations can target the olfactory cleft with its mucosa facing either upside-down or upright.

In some embodiments, the compositions are in particle form. In some embodiments, the compositions are in the form of nanoparticles. The use of nanoparticles as drug delivery systems allows controlled and site-specific delivery of therapeutic agents. Nanoparticles are able to protect the drug from biological or chemical degradation and help to evade drug-efflux mechanisms such as P-glycoprotein transporter in the blood-brain barrier, due to encapsulation of the drug. The use of nano- and microparticles for drug delivery brings along some benefits, such as a controlled and sustained drug release or by shielding the drug against environmental influences. Nanocarriers for drug delivery systems include, but are not limited to, polymeric, lipid and inorganic nanoparticles. Biodegradable drug carriers as poly lactic acid (PLA), poly glycolic acid (PGA) and their polymer poly(lactid-co-glycolid) acid (PLGA) are suitable for use in intranasal delivery.

In some embodiments, the compositions are lipid-based compositions. Lipid-based compositions can comprise lipid-based carriers such as mono-, di-, triglycerides, fatty acids and waxes. Nanostructured lipid carriers can be composed of blends of solid and liquid state lipids.

A composition of the disclosure can be, for example, an immediate release form. An immediate release formulation can be formulated to allow a compound to act rapidly. Non-limiting examples of immediate release formulations include readily dissolvable formulations.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Compounds can be delivered via liposomal technology. The use of liposomes as drug carriers can increase the therapeutic index of a compound. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues.

Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

A pharmaceutical composition of the disclosure can be in the form of an aqueous solution. In some embodiments, the pharmaceutical composition can comprise from about 5% to about 10%, from about 10% to about 15%, from about 15% to about 20%, from about 20% to about 25%, or from about 25% to about 30% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 5%, about 10%, about 15%, about 20%, about 25%, or about 30% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 10%, about 11%, about 12%, about 13%, about 14%, about 15%, about 16%, about 17%, about 18%, about 19%, or about 20% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 15% of NAC, NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 20% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 25% of NAC, NACA, NAC derivative, NAC metabolite, NAC congener, or D-NAC, or a pharmaceutically-acceptable salt thereof in an aqueous solution.

A pharmaceutical composition of the disclosure can be in the form of a dry powder. In some embodiments, the pharmaceutical composition can comprise from about 5% to about 10%, from about 10% to about 15%, from about 15% to about 20%, from about 20% to about 25%, or from about 25% to about 30% of NAC, NACA, NAC derivative, NAC metabolite, NAC congener, or D-NAC, or a pharmaceutically-acceptable salt thereof in a dry powder formulation. In some embodiments, a pharmaceutical composition of the disclosure can comprise about 5%, about 10%, about 15%, about 20%, about 25%, or about 30% of NAC, NACA, NAC derivative, NAC metabolite, NAC congener, or D-NAC, or a pharmaceutically-acceptable salt thereof in a dry powder formulation. In some embodiments, a pharmaceutical composition of the disclosure can comprise about 10%, about 11%, about 12%, about 13%, about 14%, about 15%, about 16%, about 17%, about 18%, about 19%, or about 20% of NAC, NACA, NAC derivative, NAC metabolite, NAC congener, or D-NAC, or a pharmaceutically-acceptable salt thereof in a dry powder formulation. In some embodiments, a pharmaceutical composition of the disclosure can comprise about 15% of NAC, NACA, NAC derivative, NAC metabolite, NAC congener, or D-NAC, or a pharmaceutically-acceptable salt thereof in an aqueous solution. In some embodiments, a pharmaceutical composition of the disclosure can comprise about 20% of NAC, NACA, NAC derivative, NAC metabolite, NAC congener, or D-NAC, or a pharmaceutically-acceptable salt thereof in a dry powder formulation. In some embodiments, a pharmaceutical composition of the disclosure can comprise about 25% of NAC, NACA, NAC derivative, NAC metabolite, NAC congener, or D-NAC, or a pharmaceutically-acceptable salt thereof in a dry powder formulation.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Modes of Administration

A compound of the disclosure can be delivered to the nasal cavity to increase exposure of the compound at the olfactory epithelium or respiratory epithelium. In some embodiments, the compound can be propelled with a specified velocity into the nasal cavity. In some embodiments, the compound can be administered as an intranasal spray. In some embodiments, a compound can be packaged in a pressurized aerosol container with suitable propellants and adjuvants. In some embodiments, the propellant can be a fluid. The fluid can be a liquid, gas, or a combination thereof. In some embodiments, the propellant is a gas (e.g., nitrogen or chloroflourocarbons). In some embodiments, the propellant is pressurized air (e.g. ambient air). In some embodiments, the propellant is a liquid.

In some embodiments, the propellants are hydrocarbon propellants, such as propane, butane, or isobutene. In some embodiments, the propellant is hydrofluoroalkane (HFA), such as HFA, HFA 227, HFA 134a, HFA-FP, or HFA-BP. In some embodiments, aerosol formulations can include other ingredients, such as mucoadhesive agent, adsorption enhancers, co-solvents, stabilizers, surfactants, antioxidants, preservatives, lubricants, and pH adjusters. The aerosol formulations can be administered using a metered dose inhaler. The metered dose inhaler can comprise a pressurized cannister and/or a metering valve to meter the propellant or aerosol formulation upon actuation.

A compound of the disclosure can be administered as a sprayable powder. In some embodiments, a compound can be administered as an inhalable dry powder. In some embodiments, the powder formulation can include pharmaceutically acceptable excipients, such as monosaccharides (e.g., glucose, arabinose), disaccharides (e.g., lactose, saccharose, maltose), oligosaccharides or polysaccharides (e.g., dextrane, polyalcohols (e.g., sorbitol, mannitol, xylitol), salts (e.g., sodium chloride, calcium carbonate), or any combination thereof. In some embodiments, a compound can be administered as a solution, suspension, or a dry powder. In some embodiments, a compound can be administered in a non-pressurized form using a nebulizer or an atomizer.

Delivery of a compound of the disclosure as an intranasal pharmaceutical composition can result in lower systemic drug exposure and fewer side effects. In some embodiments, delivery of the compound results in no systemic drug exposure. In some embodiments, lower systemic drug exposure or no systemic drug exposure can lower the risk of bleeding, gastrointestinal side effects, liver toxicity, fluid retention or edema, neutropenia or leukopenia, anemia, or infection. In some embodiments, lower systemic drug exposure or no systemic drug exposure can lower the risk of gastrointestinal side effects, such as nausea, vomiting, or diarrhea.

A compound of the disclosure can be administered directly to the nasal cavity using an intranasal delivery device. In some embodiments, a compound can be administered intranasally in the form of a vapor or drops. In some embodiments, a compound can be administered using an intranasal delivery device, such as a rhinyle catheter, multi-dose dropper, unit-dose pipette, or vapor inhaler. In some embodiments, a compound can be delivered using a squeeze bottle, multi-dose metered-dose spray pump, single or duo-dose spray pump, or a bidirectional multi-dose spray pump. In some embodiments, a compound can be delivered using an atomizer. In some embodiments, a compound can be delivered using a nebulizer. In some embodiments, the intranasal delivery device can comprise a propellant container, formulation container, or a diffuser. In some embodiments, the intranasal delivery device can comprise a diffuser to diffuse the propellant. In some embodiments, the diffuser can be connected to a formulation container that is configured to hold the formulation. In some embodiments, the diffuser can be connected to a propellant container (e.g., a pressurized propellant container) that is configured to hold the propellant. In some embodiments, the formulation container and the propellant container are the same container. In some embodiments, the formulation container is different from the propellant container. In some embodiments, the propellant can serve as a vehicle to deliver propulsion or thrust to expel the formulation from the formulation container. In some embodiments, the formulation container is connected to a nozzle. In some embodiments, the propulsion or thrust from the propellant is capable of expelling the formulation from the formulation container and the nozzle.

In some embodiments, the diffuser can be porous. In some embodiments, the pores can be homogenous in size and shape. In some embodiments, the pores of the diffuser can be heterogeneous in size and shape. In some embodiments, the diffuser is homogenously porous. In some embodiments, the diffuser is heterogeneously porous. In some embodiments, the propellant passes through the pores, but the pores are impervious to the formulation.

In some embodiments, the diffuser is connected to the propellant. In some embodiments, the diffuser can convert a liquid propellant, exiting the propellant container, into a gaseous propellant. In some embodiments, the diffuser can increase a temperature of the resulting gas. In some embodiments, the passage of a gas propellant through the diffuser can increase the temperature of the gas propellant.

Following contact with the diffuser, the diffused propellant can come into contact with the formulation in the formulation container. The diffused propellant and the formulation can come into contact with each other as the propellant propels the formulation in the formulation container through the nozzle. Exiting from the nozzle is the aerosolized formulation, propellant, or a combination thereof. In some embodiments, the nozzle is inserted to a specified length into the subject's nasal cavity. In some embodiments, the nozzle is configured to be a separate inhalation tube that is inserted to a specified length into the subject's nasal cavity from the nostril. In some embodiments, the specified length into the subject's nasal cavity from the nostril can be at least about 0.1 cm, about 0.2 cm, about 0.3 cm, about 0.4 cm, about 0.5 cm, about 0.6 cm, about 0.7 cm, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm, or more. In some embodiments, the specified length into the subject's nasal cavity from the nostril can be about 0.1 cm, about 0.2 cm, about 0.3 cm, about 0.4 cm, about 0.5 cm, about 0.6 cm, about 0.7 cm, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2.0 cm, about 2.1 cm, about 2.2 cm, about 2.3 cm, about 2.4 cm, about 2.5 cm. In some embodiments, the specified length into the subject's nasal cavity from the nostril can be at most about 2.5 cm, about 2.4 cm, about 2.3 cm, about 2.2 cm, about 2.1 cm, about 2.0 cm, about 1.9 cm, about 1.8 cm, about 1.7 cm, about 1.6 cm, about 1.5 cm, about 1.4 cm, about 1.3 cm, about 1.2 cm, about 1.1 cm, about 1.0 cm, about 0.9 cm, about 0.8 cm, about 0.7 cm, about 0.6 cm, about 0.5 cm, about 0.4 cm, about 0.3 cm, about 0.2 cm, about 0.1 cm, or less. In some embodiments, the formulation can reach a distance in of at least about 1 cm, about 2 cm, about 3 cm, about 4 cm, about 5 cm, about 6 cm, about 7 cm, about 8 cm, about 9 cm, about 10 cm or more from the nostril. In some embodiments, the formulation can reach a distance of about 1 cm, about 2 cm, about 3 cm, about 4 cm, about 5 cm, about 6 cm, about 7 cm, about 8 cm, about 9 cm, or about 10 cm from the nostril. In some embodiments, the formulation can reach a distance of at most about 15 cm, about 14 cm, about 13 cm, about 12 cm, about 11 cm, about 10 cm, about 9 cm, about 8 cm, about 7 cm, about 6 cm, about 5 cm, about 4 cm, about 3 cm, about 2 cm, about 1 cm, or less from the nostril.

In some embodiments, the intranasal delivery device can comprise a nose aiming guide that functions to accommodate the subject's nose. In some embodiments, the nose aiming guide is configured to aim the nozzle at the subject's olfactory region. In some embodiments, the intranasal delivery device comprises a septum aiming guide that is configured to accommodate contacting the subject's septum. In some embodiments, the intranasal delivery device comprises an upper lip aiming guide configured to accommodate the subject's upper lip.

In some embodiments, a compound can be administered intranasally in the form of a powder. In some embodiments, a compound can be delivered using mechanical powder sprayer, breath actuated inhaler, or an insufflator. In some embodiments, a compound can be delivered using a mechanical powder spray device. In some embodiments, a compound can be delivered using a multi-dose powder inhaler, single or duo-dose capsule inhaler, or a nasal inhaler. In some embodiments, a compound can be delivered using an insufflator, or a breath-powered bi-directional delivery system.

In some embodiments, compound of the disclosure can be administered directly to the nasal cavity using an intranasal delivery device. In some embodiments, at least one therapeutically effective dose of the compound is delivered using the intranasal delivery device. In some embodiments, at least one therapeutically effective dose of the compound is delivered to the olfactory epithelium or respiratory epithelium.

In some embodiments, substantially all of the dose enters the nasal cavity of the subject. In some embodiments, at least about 50%, about 55%, about 60%, about 65%, about 70%, about 75%, about 80%, about 85%, about 90%, about 95%, or about 100% of the dose enters the nasal cavity of the subject. In some embodiments, about 50%, about 55%, about 60%, about 65%, about 70%, about 75%, about 80%, about 85%, about 90%, about 95%, or about 100% of the dose enters the nasal cavity of the subject. In some embodiments, at most about 100%, about 95%, about 90%, about 85%, about 80%, about 75%, about 70%, about 65%, about 60%, about 55%, about 50%, or less of the dose enters the nasal cavity of the subject.

Dosing

Pharmaceutical compositions described herein can be in unit dosage forms suitable for single administration of precise dosages. In unit dosage form, the formulation is divided into unit doses containing appropriate quantities of one or more compound. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be administered to a subject in a composition in a range of from, about 1 mg/kg to about 5 mg/kg, about 1 mg/kg to about 10 mg/kg, about 1 mg/kg to about 25 mg/kg, about 10 mg/kg to about 50 mg/kg, about 10 mg/kg to about 75 mg/kg, about 10 mg/kg to about 100 mg/kg, about 50 mg/kg to about 125 mg/kg, about 50 mg/kg to about 150 mg/kg, about 50 mg/kg to about 175 mg/kg, about 50 mg/kg to about 200 mg/kg, about 100 mg/kg to about 225 mg/kg, about 100 mg/kg to about 250 mg/kg, about 100 mg/kg to about 275 mg/kg, about 100 mg/kg to about 300 mg/kg, about 150 mg/kg to about 325 mg/kg, about 150 mg/kg to about 350 mg/kg, about 150 mg/kg to about 375 mg/kg, about 150 mg/kg to about 400 mg/kg, about 250 mg/kg to about 425 mg/kg, about 250 mg/kg to about 450 mg/kg, or about 250 mg/kg to about 500 mg/kg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some embodiments, a method of the disclosure administers a therapeutically-effective amount from about 100 mg to about 400 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg. In some embodiments, a compound described herein can be present in a composition in an amount of about 350 mg. In some embodiments, a compound described herein can be present in a composition in an amount of about 400 mg.

In some embodiments, a compound of the disclosure can be administered to a subject in a composition in an amount of about 1 mg/kg to about 10 mg/kg. In some embodiments, a compound of the disclosure can be administered to a subject in a composition in an amount of about 1-50 mg/kg. In some embodiments, a compound of the disclosure can be administered to a subject in a composition in an amount of about 1-75 mg/kg. In some embodiments, a compound of the disclosure can be administered to a subject in a composition in an amount of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dosage is administered in each nostril in equal amounts. In some embodiments, about 0.1 mL, about 0.2 mL, about 0.3 mL, about 0.4 mL, about 0.5 mL, about 0.6 mL, about 0.7 mL, about 0.8 mL, about 0.9 mL, or about 1.0 mL of a pharmaceutical composition is administered in each nostril of a subject. In some embodiments, 0.25 mL of a pharmaceutical composition is administered in each nostril per dose. In some embodiments, 0.5 mL of a pharmaceutical composition is administered in each nostril per dose.

In some embodiments, dosing is repeated for each nostril to increase the amount of a compound. In some embodiments, a first dosage of a pharmaceutical composition is about 0.1 mL, about 0.2 mL, about 0.3 mL, about 0.4 mL, about 0.5 mL, about 0.6 mL, about 0.7 mL, about 0.8 mL, about 0.9 mL, or about 1.0 mL per nostril of the subject. In some embodiments, a follow up dosage is the same amount as the first dosage of the pharmaceutical composition. In some embodiments, a follow up dosage is a different amount as the first dosage of the pharmaceutical composition. In some embodiments, the follow up dosage is a smaller amount than the first dosage of the pharmaceutical composition. In some embodiments, the follow up dosage is a greater amount than the first dosage of the pharmaceutical composition.

In some embodiments, 0.5 mL of a pharmaceutical composition is administered in each nostril per dose, and the dosing is repeated after a period of time to administer a total of 1 mL of a pharmaceutical composition per nostril. In some embodiments, a follow up dose is administered about 5 minutes after administration of the first dose. In some embodiments, 0.5 mL of a pharmaceutical composition is administered in each nostril per dose, and the dosing is repeated twice each after a period of time to administer a total of 1 mL of a pharmaceutical composition per nostril.

Therapeutic agents described herein can be administered before, during, or after the occurrence of a disease or condition, and the timing of administering the composition containing a therapeutic agent can vary. In some embodiments, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

A compound or pharmaceutical composition of the disclosure can be administered more than one time. In some embodiments, a compound or pharmaceutical composition of the disclosure can be administered once daily. In some embodiments, a compound or pharmaceutical composition of the disclosure can be administered twice daily. In some embodiments, a compound or pharmaceutical composition of the disclosure can be administered three times daily. In some embodiments, a compound or pharmaceutical composition of the disclosure can be administered, and the administration can be repeated at least once. In some embodiments, administration of a compound or a pharmaceutical composition can be repeated once. In some embodiments, administration of a compound or a pharmaceutical composition can be repeated twice. In some embodiments, administration of a compound or a pharmaceutical composition can be repeated three times.

In some embodiments, administration of a compound or a pharmaceutical composition can be repeated after about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days. In some embodiments, administration of a compound or pharmaceutical composition can be repeated after about 7 days. In some embodiments, administration of a compound or pharmaceutical composition can be repeated after about 14 days.

In some embodiments, it is advisable to administer a therapeutic agent (e.g., NAC, NACA, NAC derivative, NAC metabolite, NAC congener, or D-NAC) as soon as practical after a subject experiences brain injury, for example traumatic brain injury. In some embodiments, traumatic brain injury and/or secondary brain damage resulting from traumatic brain injury can be treated by administering the compounds and compositions of the disclosure to soldiers the compounds can be administered on site as soon as possible after a soldier experiences traumatic brain injury. In some embodiments, a compound or composition is administered about 1 minute, about 5 minutes, about 10 minutes, about 15 minutes, about 20 minutes, about 25 minutes, about 30 minutes, about 35 minutes, about 40 minutes, about 45 minutes, about 50 minutes, about 55 minutes or about 1 hour after the onset of brain injury.

Combination Therapy

The compounds or pharmaceutical compositions of the disclosure can be administered with at least one additional therapeutic agent. In some embodiments, the compounds or pharmaceutical compositions of the disclosure can be administered with one additional therapeutic agent. In some embodiments, the compounds or pharmaceutical compositions of the disclosure can be administered with two additional therapeutic agents. In some embodiments, the compounds or pharmaceutical compositions of the disclosure can be administered with three additional therapeutic agents.

Multiple therapeutic agents can be administered in any order or simultaneously. In some embodiments, a compound of the invention is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

In some embodiments, the therapeutic agent is a 5-lipogenase-activating protein (FLAP) inhibitor. In some embodiments, the FLAP inhibitor is MK-866 (L 663536), quiflapon (MK-591), fiboflapon (GSK2190915; AM-803), veliflapon (BAY X 1005; DG-031), AM679, or a pharmaceutically-acceptable salt thereof. In some embodiments, the therapeutic agent is glutathione. In some embodiments, the therapeutic agent is a glutathione-decorated nanoparticle.

In some embodiments, the therapeutic agent is a Cathepsin B inhibitor. In some embodiments, the Cathepsin B inhibitor is antipain dihydrochloride, CA-074, CA-074 methyl ester, Calpain inhibitor I, Calpain inhibitor II, chymostatin, cystatin, E-64, leupeptin trifluoroacetate salt, procathepsin B fragment, Z-Leu-Leu-Leu fluoromethyl ketone. In some embodiments, the Cathepsin B inhibitor is antipain dihydrochloride. In some embodiments, the Cathepsin B inhibitor is CA-074. In some embodiments, the Cathepsin B inhibitor is cystatin. In some embodiments, the Cathepsin B inhibitor is chymostatin.

In some embodiments, the therapeutic agent is a poly (ADP-ribose) polymerase (PARP) inhibitor. In some embodiments, the PARP inhibitor is olaparib, rucaparib, niraparib, talazoparib, veliparib, pamiparib, rucaparib, CEP 9722, E7016, Iniparib, or 3-aminobenzamide. In some embodiments, the PARP inhibitor is olaparib. In some embodiments, the PARP inhibitor is rucaparib. In some embodiments, the PARP inhibitor is niraparib. In some embodiments, the PARP inhibitor istalazoparib.

In some embodiments, the therapeutic agent is probenecid. In some embodiments, the therapeutic agent is phenserine. In some embodiments, the therapeutic agent is a dopaminergic agent.

Therapeutic Effects

Administering NAC, NACA, NAC derivative, NAC metabolite, NAC congener, or D-NAC, or a pharmaceutically-acceptable salt thereof can change the concentration of a NAC neurometabolite in a brain region. In some embodiments, the brain region is the cerebrum, brainstem, cerebellum, pons, medulla, frontal lobe, parietal lobe, occipital lobe, temporal lobe, left dorsal striatum, occipital cortex, or dorsolateral prefrontal cortex (DLPF). In some embodiments, the brain region is the occipital lobe. In some embodiments, the brain region is the occipital cortex. In some embodiments, the brain region is the cerebellum. In some embodiments, the brain region is the DLPF.

In some embodiments, the administering increases the concentration of a NAC neurometabolite in the brain region. In some embodiments, the administering increased the concentration of a NAC neurometabolite in the brain region by from about 20% to about 300%. In some embodiments, the administering increased the concentration of a NAC neurometabolite in the brain region by from about 5% to about 10%, from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100%. In some embodiments, the administering increased the concentration of a NAC neurometabolite in the brain region by from about 100% to about 110%, from about 110% to about 120%, from about 120% to about 140%, from about 140% to about 160%, from about 160% to about 180%, from about 180% to about 200%, from about 200% to about 220%, from about 220% to about 240%, from about 240% to about 260%, from about 260% to about 280%, or from about 280% to about 300%.

In some embodiments, the administering increased the concentration of a NAC neurometabolite in the brain region by about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, or about 300%. In some embodiments, the administering increased the concentration of a NAC neurometabolite in the brain region by about 20%. In some embodiments, the administering increased the concentration of a NAC neurometabolite in the brain region by about 50%. In some embodiments, the administering increased the concentration of a NAC neurometabolite in the brain region by about 100%. In some embodiments, the administering increased the concentration of a NAC neurometabolite in the brain region by about 150%. In some embodiments, the administering increased the concentration of a NAC neurometabolite in the brain region by about 200%.

In some embodiments, the administering of NAC, NACA, NAC derivative, NAC metabolite, NAC congener, or D-NAC, or a pharmaceutically-acceptable salt thereof modulates the NAC neurometabolite/water ratio in a brain region. In some embodiments, the administering of NAC, NACA, NAC derivative, NAC metabolite, NAC congener, or D-NAC, or a pharmaceutically-acceptable salt thereof modulates the GSH/water ratio in a brain region. In some embodiments, the administering of NAC, NACA, NAC derivative, NAC metabolite, NAC congener, or D-NAC, or a pharmaceutically-acceptable salt thereof increases the GSH/water ratio in a brain region. In some embodiments, the administering of NAC, NACA, NAC derivative, NAC metabolite, NAC congener, or D-NAC, or a pharmaceutically-acceptable salt thereof modulates the NAA/water ratio in a brain region. In some embodiments, the administering of NAC, NACA, NAC derivative, NAC metabolite, NAC congener, or D-NAC, or a pharmaceutically-acceptable salt thereof increases the NAA/water ratio in a brain region.

In some embodiments, the administering of NAC, NACA, NAC derivative, NAC metabolite, NAC congener, or D-NAC, or a pharmaceutically-acceptable salt thereof increases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/water ratio in a region of the brain by about 10%. In some embodiments, the administering increases the GSH/water ratio in a region of the brain by about 20%. In some embodiments, the administering increases the GSH/water ratio in a region of the brain by about 30%. In some embodiments, the administering of NAC, NACA, NAC derivative, NAC metabolite, NAC congener, or D-NAC, or a pharmaceutically-acceptable salt thereof decreases the GSH/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/water ratio in a region of the brain by about 10%. In some embodiments, the administering decreases the GSH/water ratio in a region of the brain by about 20%. In some embodiments, the administering decreases the GSH/water ratio in a region of the brain by about 30%.

In some embodiments, the administering of NAC, NACA, NAC derivative, NAC metabolite, NAC congener, or D-NAC, or a pharmaceutically-acceptable salt thereof increases the NAA/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/water ratio in a region of the brain by about 10%. In some embodiments, the administering increases the NAA/water ratio in a region of the brain by about 20%. In some embodiments, the administering increases the NAA/water ratio in a region of the brain by about 30%. In some embodiments, the administering of NAC, NACA, NAC derivative, NAC metabolite, NAC congener, or D-NAC, or a pharmaceutically-acceptable salt thereof decreases the NAA/water ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the NAA/water ratio in a region of the brain by about 10%. In some embodiments, the administering decreases the NAA/water ratio in a region of the brain by about 20%. In some embodiments, the administering decreases the NAA/water ratio in a region of the brain by about 30%.

In some embodiments, the administering of NAC, NACA, NAC derivative, NAC metabolite, NAC congener, or D-NAC, or a pharmaceutically-acceptable salt thereof modulates the NAC neurometabolite/creatine ratio in a brain region. In some embodiments, the administering of NAC, NACA, NAC derivative, NAC metabolite, NAC congener, or D-NAC, or a pharmaceutically-acceptable salt thereof modulates the GSH/creatine ratio in a brain region. In some embodiments, the administering of NAC, NACA, NAC derivative, NAC metabolite, NAC congener, or D-NAC, or a pharmaceutically-acceptable salt thereof increases the GSH/creatine ratio in a brain region. In some embodiments, the administering of NAC, NACA, NAC derivative, NAC metabolite, NAC congener, or D-NAC, or a pharmaceutically-acceptable salt thereof modulates the NAA/creatine ratio in a brain region. In some embodiments, the administering of NAC, NACA, NAC derivative, NAC metabolite, NAC congener, or D-NAC, or a pharmaceutically-acceptable salt thereof increases the NAA/creatine ratio in a brain region.

In some embodiments, the administering of NAC, NACA, NAC derivative, NAC metabolite, NAC congener, or D-NAC, or a pharmaceutically-acceptable salt thereof increases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the GSH/creatine ratio in a region of the brain by about 10%. In some embodiments, the administering increases the GSH/creatine ratio in a region of the brain by about 20%. In some embodiments, the administering increases the GSH/creatine ratio in a region of the brain by about 30%. In some embodiments, the administering of NAC, NACA, NAC derivative, NAC metabolite, NAC congener, or D-NAC, or a pharmaceutically-acceptable salt thereof decreases the GSH/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the GSH/creatine ratio in a region of the brain by about 10%. In some embodiments, the administering decreases the GSH/creatine ratio in a region of the brain by about 20%. In some embodiments, the administering decreases the GSH/creatine ratio in a region of the brain by about 30%.

In some embodiments, the administering of NAC, NACA, NAC derivative, NAC metabolite, NAC congener, or D-NAC, or a pharmaceutically-acceptable salt thereof increases the NAA/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering increases the NAA/creatine ratio in a region of the brain by about 10%. In some embodiments, the administering increases the NAA/creatine ratio in a region of the brain by about 20%. In some embodiments, the administering increases the NAA/creatine ratio in a region of the brain by about 30%. In some embodiments, the administering of NAC, NACA, NAC derivative, NAC metabolite, NAC congener, or D-NAC, or a pharmaceutically-acceptable salt thereof decreases the NAA/creatine ratio in a region of the brain by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the administering decreases the NAA/creatine ratio in a region of the brain by about 10%. In some embodiments, the administering decreases the NAA/creatine ratio in a region of the brain by about 20%. In some embodiments, the administering decreases the NAA/creatine ratio in a region of the brain by about 30%.

In some embodiments, administering NAC, NACA, NAC derivative, NAC metabolite, NAC congener, or D-NAC, or a pharmaceutically-acceptable salt thereof can increase a GSH/creatine ratio and decrease an NAA/creatine ratio in a region of the brain. In some embodiments, administering NAC, NACA, NAC derivative, NAC metabolite, NAC congener, or D-NAC, or a pharmaceutically-acceptable salt thereof can increase a GSH/creatine ration by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%; and decrease an NAA/creatine ratio by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% in a region of the brain.

Subjects

A subject disclosed herein can be, for example, an elderly adult, an adult, an adolescent, a pre-adolescent, a child, a toddler, an infant, a neonate, and non-human animals. In some embodiments, a subject is a patient.

Clinical Assessment Tools

Disclosed herein are methods for quantifying and measuring intranasal NAC or GSH uptake. In some embodiments, nose-to-brain NAC or GSH administration is measured using direct continuous cerebrospinal fluid (CSF) monitoring, mathematical modeling, or other analytical techniques that can non-invasively monitor local drug or metabolite levels within the CNS. In some embodiments, physiologic phenomena reflective of localized CNS-mediated NAC or GSH bioactivity is measured after nose-to-brain NAC or GSH administration to document or calibrate nose-to-brain delivery in subjects. In some embodiments, nose-to-brain NAC or GSH administration is quantified and measured using positron emission tomography (PET), single-photon emission computed tomography (SPECT), gamma scintigraphy, bio-luminescence imaging (BLI), fluorescence imaging (FLI), ultrasound imaging and ultrasound transducers, computed tomography, optical imaging, nuclear magnetic resonance (NMR) techniques, such as magnetic resonance spectroscopy (MRS) or magnetic resonance imaging (MRI), or a combination thereof.

In some embodiments, nose-to-brain NAC or GSH administration is quantified and measured using MRS or MRI. MRI is a non-ionizing imaging technology that utilizes a strong magnet to produce three-dimensional detailed anatomical high spatial images and exquisite soft tissue contrast. Image contrast in MRI is based on inherent properties of biologic tissues (e.g., proton content, longitudinal recovery time, transverse relaxation times). In some embodiments, contrast agents, such as gadolinium-based contrast agents (e.g., gadolinium-diethylenetriamine-pentaacetic acid (Gd-DTPA)) and iron-containing agents can be utilized for contrast enhancement and image brightening. In addition to static imaging, MRI can collect dynamic information using various perfusion techniques. In some embodiments, perfusion techniques can include dynamic susceptibility contrast, dynamic contrast enhancement, or arterial spin labeling. In some embodiments, MRS, an ionizing radiation-free analytical technique, can be used alone or in combination with MRI, for quantifying and measuring nose-to-brain NAC or GSH administration.

Several tools can also be utilized to diagnose and assess the clinical and neuropsychological features of CNS conditions. In some embodiments, standard physical and neurological examinations, and neuropsychometric tests can be used to diagnose and assess a subject with a CNS condition.

Biomarkers and imaging: Electrophysiological techniques, imaging techniques, and blood tests can be used to assess the CNS condition of a subject. Event-related potentials (EPRs) can be used to evaluate computer-processed electroencephalogram (EEG) signals time-locked to a perpetual or cognitive task. In some embodiments, computed tomography (CT) and magnetic resonance imaging (MRI) can be used to diagnose or track the progress of a CNS condition. In some embodiments, diffusion tensor imaging can be used to diagnose or track the progression of a CNS condition.

In some embodiments, MRI can be used to determine the levels of metabolites in the brain and assess the progress of a CNS disease. In some embodiments, MRI can be used to quantify metabolite levels in the range of μmoles/g, such as N-acetylaspartate, lactate, glutamate, gamma-aminobutyric acid, and glutathione.

Post-concussion symptom score (PCSS): The PCSS score contains 22 items that can be used to evaluate symptoms of a concussion in a subject on a 7-point scale. O correlates to no symptoms, and 6 correlates to severe symptoms. PCSS scores can be used in subjects ages 11 and above in identifying individuals with clinically-diagnosed concussion, and in predicting prolonged recovery.

Graded symptom checklist (GSC): The GSC contains 16 items scored on a 7-point scale. The GSC scale is applicable to subjects ages 13 and above, and incorporates a three-factor structure (cognitive, somatic, and neurobehavioral).

Standardized concussion assessment tool (SCAT): SCAT is a standardized tool that incorporates other assessment scales, such as GCS, Maddocks questions for memory assessment, PCSS, and other neurological and cognitive tests.

Immediate post-concussion assessment and cognitive testing (ImPACT): ImPACT is a computerized test battery with 3 components, such as demographic data, neuropsychological testing, and PCSS. ImPACT includes assessments of cognition (e.g., attention, processing speed, impulsivity, and reaction time). In a combination with a scale for mTBI symptoms, ImPACT has a sensitivity of 81.9%, and a specificity of 89.4%.

King-Devick Scale: The King-Devick scale is a brief test administered acutely following head injury in which the subject must read patterns of letters and numbers on test cards. The King-Devick scale assess language, attention, and eye movements, all of which can be impaired in a CNS condition, for example, after a concussion.

EXAMPLES

Example 1: Phase I Study of Brain Bioavailability and Safety of Intranasal NAC

A single site, single-blind, and open label six-part Phase 1 study in healthy volunteers is conducted to assess the brain bioavailability, safety, and tolerability of IN NAC utilizing 1H-MRS measurement of NAC-derived neurometabolites. Brain bioavailability of NAC-derived neurometabolites is assessed for three doses of IN NAC and compared to the effects of IN GSH. Additionally, the effect of different formulations, dosing devices, and positioning during IN administration are evaluated. Comparative brain bioavailability of NAC is measured following administration of NAC via IN, IV, or oral administration. The effects of 7-day repeat dosing of NAC via IN, IV, or oral administration are determined using 1H-MRS.

Measurements are obtained pre-dose and post-dose 1H-MRS of NAC-derived brain metabolites during single ascending and repeat dose studies of IN NAC. Blood levels of NAC (free and total), cysteine, GSH and GSH/GSSG ratios are also obtained, and measurements of cerebrospinal fluid (CSF) NAC are obtained before and after 7 days of repeat dosing. Safety and tolerability are assessed through reports of adverse events, findings on physical neurologic examinations, laboratory test results, findings on the electrocardiogram (ECG), and specific assessment for nasal tolerability.

For each part of the study, participants undergo screening beginning up to 28 days prior to IP administration on Day 1. Subjects are required to sign an informed consent form (ICF) before undertaking any study-specific procedures or assessments. Participants who qualify for the study based on inclusion and exclusion criteria are enrolled. In each part of the study, safety is monitored by assessment of adverse events (AEs), vulnerability assessment scoring tool (VAS-T), and modified total nasal symptom (TNSS-M) scores, electrocardiogram (ECG) results, vital signs, physical and neurological examinations, blood tests and urine tests.

The pharmacokinetic (PK) and pharmacodynamic (PK) properties of a single dose of IN GSH and single ascending doses of IN NAC are determined by measuring the effect of the doses on NAC-derived neurometabolites as assessed by 1) 1H-MRS measurements of the N-cysteinyl resonances of GSH and NAC and the N-acetyl resonances of NAC and N-acetyl aspartate (NAA), expressed as ratios to the water or creatine resonance of voxels in the dorsolateral prefrontal cortex (DLPF), occipital lobe and striatum; and 2) peripheral blood concentrations of GSH, free and total NAC, cysteine and RBC GSH/GSSH ratios. In each part of the study, MRS analysis is completed and PK samples are drawn pre-dose and at 1, 3, 6, and 24 hours post-dose.

The effects of IN NAC administered under different dosing conditions, formulations, using different devices, and participant positioning during IP administration are determined by measuring NAC-derived neurometabolites in the voxels of interest using MRS. The effects of twice-daily dosing of IN NAC for 7 days on MRS-determined levels of 1) the aforementioned NAC-derived neurometabolites in the voxels of interest, 2) CSF NAC levels, and 3) peripheral blood concentrations of GSH, free and total NAC, cysteine and RBC GSH/GSSH ratios are measured.

Participant population: The study is conducted in 72 healthy male and female volunteers, inclusive at the time of informed consent. Women of childbearing potential (WOCBP) may be included and are subject to contraceptive requirements during the study from screening until study completion, including the follow-up period, and for at least 90 days after the last dose of IP. WOCBP must demonstrate negative pregnancy testing at screening and before administration of IP. The maximum duration of involvement for each participant, screening through study completion, is approximately 64-78 days.

Inclusion criteria: 1) Healthy volunteers between 18 and 45 years of age inclusive at the time of informed consent; 2) In good general health as determined by medical history, physical examination, vital signs, laboratory tests, and ECG. Isolated out-of-range values judged by the Principal Investigator (PI) or designated physician to be of no clinical significance can be allowed: the rationale for this determination must be recorded in the participant's source documents; 3) Have a body weight in the range of 50 to 120 kg, inclusive, and a body mass index (BMI) of 19 to 28 kg/m$^2$, inclusive, at screening; 4) Agree to abstain from alcohol intake for 24 hours prior to IP administration and 24 hours prior to all other outpatient clinic visits; 5) Agree not to use prescription medications (except for birth control) within 14 days prior to IP administration and for the duration of the study, unless approved by the PI and Sponsor Medical Monitor; 6) Agree not to use over the counter (OTC) medications (including corticosteroids, aspirin, pain medications, decongestants, antihistamines) and herbal medication (including St. John's Wort) within 14 days prior to IP administration through to the Day 7 follow-up visit, unless approved by the Medical Monitor. Occasional use of paracetamol (up to 2 g/day) is permitted; 7) Agree to refrain from participation in a competitive collision sport from the initiation of the screening period to the Day 28 follow up; 8) WOCBP must be non-pregnant and must use an acceptable, highly effective double barrier contraception from Screening until study completion, including the follow-up period. Double barrier contraception is defined as use of a condom (male or female, by self-declaration) AND one form of the following: established hormonal contraception (e.g., oral contraceptives pills [OCPs], long-acting implantable hormones, injectable hormones); a vaginal ring or an intrauterine device [IUD]); documented evidence of surgical sterilization at least 6 months prior to Screening (e.g., tubal occlusion, hysterectomy, bilateral salpingectomy, or bilateral oophorectomy); WOCBP who are in same-sex or not in any sexual relations (abstinence from heterosexual intercourse, by self-declaration) are not required to use contraception when this is their preferred and usual lifestyle. These WOCBP must agree to use the aforementioned acceptable, highly effective contraceptive method if they begin or plan to begin heterosexual relations from Screening until 90 days after the last dose of study drug. WOCBP must have a negative pregnancy test at Screening and Day −1 and be willing to have additional pregnancy tests as required throughout the study.

Women not of childbearing potential (non-WOCBP) must be postmenopausal for ≥12 months. Postmenopausal status is be confirmed through testing of follicle-stimulating hormone (FSH) levels ≥40 IU/mL at Screening for amenorrhoeic female participants. Non-WOCBP are not required to use contraception. Periodic abstinence (e.g., calendar, ovulation, symptothermal, post-ovulation-methods) and withdrawal are not considered highly effective methods of birth control. Male participants engaged in sexual relations with WOCBP must use an acceptable, highly effective double barrier contraceptive method from Screening until at least 90 days after the last dosing of study drug. Double barrier contraception is defined as use of a condom (male or female, by self-declaration) and, for WOCBP, use (by self-declaration) of an effective contraceptive including OCPs, long-acting implantable hormones, injectable hormones, a vaginal ring or an IUD (by self-declaration) or having received surgical sterilization (e.g., tubal occlusion, hysterectomy, bilateral salpingectomy, or bilateral oophorectomy).

Men in same-sex or not in any sexual relations (abstinence from heterosexual intercourse, by self-declaration) are not required to use contraception if this is their preferred and usual lifestyle. These men must agree to use the aforementioned acceptable, highly effective contraceptive method if they begin or plan to begin heterosexual relations with WOCBP from Screening until 90 days after the last dosing of study drug.

Exclusion criteria: 1) Females who are pregnant or nursing at Screening; 2) Have a deformity of the nasal cavity, a known deviation of the nasal septum; acute or chronic sinusitis or recent (<5 years) history of surgery of the nasal cavity and/or nasopharynx; 3) History of seizures or epilepsy within the past 5 years; 4) History of moderate to severe traumatic brain injury; 5) History of concussion within the past 1 year; 6) Currently have or have a history of any clinically significant medical illness or medical disorders the Investigator considers should exclude the participant, including (but not limited to) cardiovascular, neurologic, musculoskeletal, hematologic, respiratory, dermatologic, hepatic or neoplastic disease or immune deficiency state; 7) Psychiatric or behavioral condition which would compromise participation in the study; 8) Acute upper respiratory illness including a common cold, within 14 days prior to IP administration or have had a major illness or hospitalization within 1 month of Screening; 9) Major surgery within 12 weeks of Screening; 10) Any participant who plans to undergo elective surgery within 4 weeks prior to IP administration and through the end of the study including the follow-up period; 11) Positive serology test for HIV antibodies, hepatitis B surface antigen (HBsAg), or hepatitis C virus (HCV) antibodies at Screening; 12) Recent history (within previous 6 months) of alcohol or drug abuse; 13) Have smoked tobacco or related products within 3 months prior to dosing; 14) Have positive urine drug test at Screening and/or at any time during the study for substances of abuse including but not limited to cocaine, cannabinoids, amphetamines, benzodiazepines, opiates, tricyclic antidepressants, and methadone. Participants can be re-screened once following a positive result at the discretion of the Investigator; 15) Have a positive alcohol breath test at Screening and/or at any time during the study. Patients are required to abstain from alcohol for at least 24 hours prior to IP administration on Day 1 and on the day of study assessments; 16) Consume, on average, more than approximately 500 mg/day of caffeine (as contained in 5 cups of tea or coffee or 8 cans of soda or other caffeinated products) per day; 17) Donated blood within 60 days prior to Screening; 18) Have a history of active drug and/or food allergy or other active allergic disease requiring the constant use of medications, or a history of severe allergic reaction, angioedema or anaphylaxis; 19) Received any other experimental therapy including device or an investigational agent within 30 days or 5 half-lives (whichever is longer) of IP administration; 20) Are unable to undergo MRI scanning due to the presence of non-removable metal implants, including but not limited to surgical staples, pacemaker, steel IUD etc., claustrophobia or any other contraindication.

Statistical Methods

Pharmacokinetics: Changes in MRS spectra of the targeted metabolites and pharmacokinetic assessments (free and total NAC, cysteine and GSH concentrations and GSH/GSSG ratios and CSF NAC levels) from baseline to each post-dose timepoint are summarized using descriptive statistics.

Safety and tolerability: Participants provide a rating for IP tolerability several times during the study using a Visual Analog Scale (VAS), with a value of 0 indicating very good tolerability and 10 indicating very poor tolerability. The subjects also complete a TNSS-M, which assesses five specific nasal symptoms (i.e., congestion, runny nose, itching, pain and non-painful burning) on a 0 to 3 scale. Only items scored as a "3" (severe) on the TNSS-M are reported as adverse events.

Adverse events are coded using the most current version of the Medical Dictionary for Regulatory Activities (MedDRA®). A by-participant AE data listing, including verbatim term, preferred term (PT), system organ class (SOC), severity and relationship to IP, are provided. The number of participants experiencing treatment emergent adverse events (TEAEs), and the number of individual TEAEs are summarized by SOC, PT, and severity and relationship to IP. Laboratory evaluations, vital signs assessments, and ECG parameters are summarized for each scheduled visit. A summary of change from baseline at each protocol specified time point are presented.

Prior and concomitant medications are coded using the most current version of the World Health Organization (WHO) drug dictionary available at the start of the study and are listed by participant and summarized by treatment using anatomical therapeutic chemical (ATC) (level 2) and preferred name. Medical history, pregnancy/FSH testing, urine drug screen/alcohol breath test, physical and neurological examination, and serology (HIV, Hepatitis B and C screen) are listed by participant.

Primary objective: The primary objective of the study is to assess the brain bioavailability of intranasal (IN) NAC using proton magnetic resonance spectroscopy (1H-MRS) assessment of change from baseline in NAC-derived metabolic markers in healthy adult volunteers.

Secondary objectives: The secondary objectives of the study include: 1) Assessing the safety and tolerability of IN NAC; 2) Assessing the time course and regional CNS pharmacodynamic activity of IN NAC; 3) Comparing pharmacokinetic and pharmacodynamic activity of IN NAC to IN GSH; 4) Comparing devices and positioning during investigational product (IP) administration for optimal nose-to-brain delivery of IN NAC; 5) Assessing the regional CNS pharmacodynamic activity and safety and tolerability of IN NAC following multiple repeated IN dose; and 6) Assessing the pharmacokinetic profile of NAC in blood and cerebrospinal fluid (CSF) following IN administration.

Screen failures: Screen failures are defined as volunteers who consent to participate in the clinical study but are not subsequently enrolled. A minimal set of screen failure information is required to ensure transparent reporting of screen failure participants to meet the Consolidated Standards of Reporting Trials publishing requirements and to respond to queries from regulatory authorities. Minimal information includes screen failure details, eligibility criteria, and any serious adverse event (SAE). Individuals who do not meet the criteria for participation in this study (screen failure) are re-screened based on the judgement of the Investigator and in consultation with the medical monitor (MM). Re-screening is allowed within the recruitment period for the study. Re-screened participants are assigned the same participant number as for the initial Screening.

Participant replacement: Participants who sign the informed consent form (ICF) and are enrolled but do not receive IP may be replaced. Participants who sign the ICF, are enrolled and receive IP but subsequently withdraw, or are withdrawn or discontinued from the study, are replaced at the discretion of the Sponsor.

Participant withdrawal criteria: Participants can withdraw their consent to participate in the study at any time. If a participant withdraws consent, the date and reason for consent withdrawal are documented. Participants are encouraged to remain in the clinic to complete all necessary assessments and until the Investigator deems that it is safe to be discharged. Participant data are included in the analysis up to the date of the withdrawal of consent.

The primary reason for withdrawal is identified and recorded on the appropriate eCRF, along with the date of withdrawal. In accordance with applicable regulations, a participant has the right to withdraw from the study, at any time and for any reason, without prejudice to future medical care. If a participant is withdrawn because of an AE, the Investigator arranges for the participant to have appropriate follow-up care until the AE is resolved or has stabilized. Unresolved AEs are followed until the last scheduled Follow-up visit or until the PI and MM determine that further follow-up is no longer indicated. In addition to AEs, other reasons for removal of participants from the study can include, but are not limited to, withdrawal of consent, administrative decision by the Investigator or the Sponsor, protocol deviation, or participant noncompliance.

If a participant asks or decides to withdraw from the study, all efforts are made to complete and report the observations, especially the listed primary and secondary objectives, as thoroughly as possible up to the date of withdrawal. Wherever possible, the tests and evaluations, including those listed for the Follow-up Visit, are performed for all participants who discontinue prior to the completion of the study.

Participant termination criteria: Reasons for early termination of individual participants can include: Protocol deviations or participant non-compliance (must be specified on the appropriate electronic case report form [eCRF]); Pregnancy; Serious or severe AEs; Administrative decision by the Investigator or the Sponsor; Death; or Other (must be specified).

Lost to follow-up: A participant is considered lost to follow-up if they fail to return for one of the scheduled visits and is unable to be contacted by the study staff. The following actions are taken if a participant fails to return for a required study visit: The site attempts to contact the participant and reschedule the missed visit within 2 days and counsel the participant on the importance of maintaining the assigned visit schedule and ascertain if the participant wishes to continue in the study. Before a participant is deemed lost to follow-up, the Investigator or designee makes every effort to regain contact with the participant (three telephone calls and contact via email and text message). These contact attempts are documented in the participant's medical record or study file. The participant is considered to have withdrawn from the study with a primary reason of lost to follow-up if the staff cannot contact the participant.

Example 2: Investigational Product, Dosage, and Mode of Administration

Participants receive one or more of IP formulation and dosage of NAC. A dose of IN NAC yielding an increase in brain GSH of approximately 13% is considered the minimal effective dose.

Intranasal NAC: For IN administration of NAC, a 20% aqueous NAC solution for inhalation or equivalent is administered intranasally at the following doses: i) 100 mg (0.5 mL)—approximately 0.25 mL in each nostril per dose; ii) 200 mg (1.0 mL)—approximately 0.50 mL in each nostril per dose; or iii) 400 mg (2.0 mL)—approximately 0.50 mL once in each nostril, with repeat administration after 5 minutes. The 20% NAC solution is supplied as a clear, colorless solution in 4 mL or 30 mL glass vials. The solution contains 200 mg/mL (20% w/v) acetylcysteine, with disodium edetate, sodium hydroxide and water. The product can also contain hydrochloric acid for pH adjustment. The pH is maintained in the range of 6.0-7.5. The NAC 20% solution is administered via one of two devices: a) Teleflex LMAR MAD Nasal™ Intranasal Mucosal Atomization Device; or b) Aptar CPS 5-mL Nasal Pump.

Intranasal GSH: For IN administration of GSH, a 20% aqueous GSH solution or equivalent is administered intranasally at a dose of 200 mg (1.0 mL), approximately 0.50 mL in each nostril. IN GSH is administered using a Teleflex MAD device.

Oral NAC: For oral administration of NAC, a 200 mg/mL NAC solution (20% w/v) is used. NAC for oral administration is prepared by diluting 20 mL of a 20% NAC solution in 60 mL of a diet soft drink, which provides a dose of 4,000 mg of NAC in a 5% solution.

IV NAC: An NAC 200 mg/mL solution for injection or equivalent is used for IV administration. The amount of NAC solution equivalent to 150 mg/kg NAC is diluted in 200 mL of 0.45% saline solution and is administered by IV over 1 hour. NAC (acetylcysteine) injection, 200 mg/mL is provided as a clear, colorless, sterile solution containing 20% w/v acetylcysteine in 30 mL vials. The solution also contains sodium hydroxide for pH adjustment and sterile water for injection.

Devices for administration: The IP is administered using: 1) an LMAR MAD Nasal™ Intranasal Mucosal Atomization Device; or 2) an Aptar CPS 5-mL Nasal Pump.

Investigational product storage: Upon receipt, the acetylcysteine 20% solution for inhalation is stored at controlled room temperature in an area protected from light and maintained at a temperature below 25° C. Remaining undiluted solution in opened vials are stored under refrigeration and used within 96 hours. The GSH solution is stored at controlled room temperature. Unopened IV NAC solutions are stored at controlled room temperature, and previously opened IN NAC vials are not used for IV administration.

Example 3: Study Evaluations and Measurements

Pharmacodynamic assessments: Pharmacodynamic assessments include change from baseline in NAC-derived neurometabolite concentrations in three brain regions (i.e., occipital cortex, striatum and DLPF), using 1H-MRS following a single dose of IN NAC in healthy volunteers at 1, 3, 6 and 24 hours post-dose.

1H-MRS analysis is performed using 3.0 cm×3.0 cm×2.5 cm voxels placed in the left dorsal striatum at the level of the lentiform nucleus, the occipital cortex, and the dorsolateral prefrontal cortex (DLPF). A J-edited spin echo difference method is implemented with an echo time (TE) of 70 ms and a repetition time (TR) of 1500 ms using 240 interleaved excitations (480 total) for an acquisition time of 12.5 minutes per voxel. A pair of frequency-selective inversion pulses are inserted into the standard point-resolved spectroscopy method and applied on alternate scans at the frequency of the reduced form of glutathione α-cysteinyl resonance at 4.56 ppm while avoiding excitation of the oxidized form of glutathione α-cysteinyl resonance at 3.28 ppm. Subtracting the two, resulting inverted subspectra of GSH yield a 1H-MRS only consisting of GSH β-cysteinyl resonance at 2.98 ppm. The 32-channel phased-array coil GSH data are combined into a single regular time-domain free-induction decay signal using the unsuppressed voxel tissue water signal from each receiver coil element to derive the required relative phased-array coil sensitivities. The metabolite concentrations are estimated by calculating the areas of the individual spectral peaks obtained by frequency-domain fitting each resonance to a Gauss-Lorentz lineshape function using the Levenberg-Marquardt non-linear least-squares algorithm.

Pharmacokinetic assessments: Pharmacokinetic assessments include peripheral blood measurements of GSH, cysteine, free and total NAC and reduced-to-oxidized GSH ratio (GSH/GSSG) ratios at 1, 3, 6, and 24 hours following IN NAC or GSH administration, and levels of CSF NAC obtained via lumbar puncture 6 hours following IP administration in Parts 5 and 6 of the study.

Blood PK sample collection: Blood PK samples are collected as close as possible prior to the acquisition of MRS data at each time point specified in the Schedule of Assessments. Blood PK measures free and total NAC, cysteine and GSH concentrations and GSH/GSSG ratio. GSH/GSSG is measured in whole blood using high performance liquid chromatography (HPLC) coupled to a mass spectrometer (MS). Total protein-bound and total protein-unbound concentrations of NAC, Cys and GSH are measured in plasma using a validated HPLC-MS assay.

Pharmacodynamic endpoints: MRS of NAC-derived brain metabolites in three regions of interest (occipital cortex, striatum, DLPF) at baseline and at 1, 3 and 6 hours following IN NAC are summarized using descriptive statistics. Change from baseline to each post-dose measurement are summarized descriptively. No a priori inferential statistical tests are planned. Brain regions of interest and timing of MRS are modified based on initial results.

Pharmacokinetic endpoints: A descriptive summary of the quantifiable concentrations of the targeted metabolites are reported for the specified time points to assess free and total NAC, cysteine and GSH concentrations and reduced-to-oxidized GSH ratio (GSH/GSSG).

Safety and tolerability: All safety assessments, including prior and concomitant medications, AEs, laboratory evaluations, vital signs, ECGs, and other safety assessments are summarized using the Safety Population.

Prior and concomitant medication: Prior and concomitant medications are coded using the most current version of the WHO drug dictionary available at the start of the study. Prior and concomitant medications are listed by participant and summarized by treatment using ATC (level 2) and preferred name.

Adverse events: Adverse events recoded using the most current version of the MedDRA available. A by participant AE data listing, including verbatim term, PT, SOC, severity and relationship to IP, are provided. The number of participants experiencing TEAEs, and the number of individual TEAEs are summarized by SOC, PT, severity and relationship to IP.

Other safety assessments: Other safety assessments listed by participant include: medical history, pregnancy test, urine drug screen, alcohol breath test, physical and neurological examination, and serology (e.g., HIV, Hepatitis B, Hepatitis C).

Safety parameters: Study procedures are completed as delineated in the Schedule of Assessments. If a participant is unable to attend a visit within the specified window, the Investigator or designee discusses appropriate scheduling with the Sponsor's MM or appropriate designee. Any unscheduled procedures required for urgent evaluation of safety concerns take precedence over all routine scheduled procedures.

Demographic and medical history: Medical history (e.g., concomitant mediations, alcohol and smoking status, and drug use), date of birth, age (calculated), sex, ethnicity, and race are recorded at Screening.

Vital signs: Vital signs (e.g., blood pressure [systolic and diastolic], pulse rate, respiratory rate, and body temperature) are listed and summarized at protocol specified collection time point. Observed and change from baseline are summarized at each protocol specified collection time point. When the time of vital signs measurement coincides with a blood draw, the vital signs are taken before the scheduled blood draw where possible, ensuring the blood draw is within the window specified in the protocol. Additional vital signs are performed at other times if deemed necessary.

Weight and height: Body height and body weight are measured at Screening and are used to calculate BMI. BMI is calculated by dividing the participant's body weight in kilograms by the participant's height in meters squared ($kg/m^2$). Body weight and height are obtained with the participant's shoes and jacket or coat removed.

Physical and neurological examination: Full and brief physical and neurological examinations are performed by a licensed physician at the time points specified in the Schedule of Assessments. Full physical examinations include: general appearance, head, ears, eyes, nose, throat, dentition, thyroid, chest (heart, lungs), abdomen, skin, neurological, extremities, back, neck, musculoskeletal, and lymph nodes. The neurological examination includes assessment of mental status and function of cranial nerves, motor and sensory systems, gait/coordination and deep tendon reflexes. Brief physical examination includes: head, ears, eyes, nose, throat, chest (heart, lungs), abdomen, skin, musculoskeletal, and lymph nodes and any pertinent system based on any prior findings. Brief neurologic examination includes assessment of eye movements, facial symmetry, drift of upper extremities, coordination (finger-to-nose and heel-toe testing) and deep tendon reflexes. Physical and neurological examinations are performed at various unscheduled time points if deemed necessary by the Investigator.

Tolerability assessments: Participants provide a rating for IP tolerability at specified times during the study using VAS-T with a value of 0 indicating very good tolerability and 10 indicating very poor tolerability. Participants also complete TNSS-M, which assesses five specific nasal symptoms (congestion, runny nose, itching, pain and non-painful burning) on a 0 to 3 scale. Only items scored as a "3" (severe) on the TNSS-M are reported as adverse events.

Electrocardiograms: ECG values are listed and summarized at protocol specified collection time point. Observed and change from baseline are summarized at each protocol specified collection time point. A 12-lead ECG are taken at the time points delineated in the Schedule of Assessments. Additional ECG monitoring are performed at other times if deemed necessary. ECGs are performed prior to vital signs with participants in a supine position.

Participants are in supine position for at least 5 minutes before the reading is taken. All ECG tracings are reviewed by the PI or designee. When the time of ECG monitoring coincides with a blood draw, the ECG is taken before the scheduled blood draw while ensuring the blood draw is within the window specified in the protocol.

Laboratory evaluations: Laboratory evaluations, including hematology, serum chemistry and urinalysis, are listed and summarized at each protocol specified collection time point. Observed and change from baseline clinical laboratory data are summarized at each protocol specified collection time point. A blood sample for safety laboratory testing (hematology, serum chemistry, and urinalysis) are taken at the time points specified in the Schedule of Assessments.

Additional clinical laboratory tests are performed at other times if deemed necessary based on the participant's clinical condition.

Hematology parameters tested are: hemoglobin (HGB); hematocrit (HCT); erythrocytes (RBC); platelets (PLAT); leukocytes with differential, including Eosinophils (ESN), Neutrophils (NEUT), Basophils (BASO), Lymphocytes (LYM), and Monocytes (MONO). Serum chemistry parameters tested are: urea (BUN); creatinine (CREAT); total Bilirubin (BILI) and Direct Bilirubin (BILIDIR); urate (URATE); albumin (ALB); globulin (GLOBUL); alkaline Phosphatase (ALP); creatine Kinase (CK); aspartate Aminotransferase (AST); alanine Aminotransferase (ALT); gamma-GT (GGT); glucose (GLU); sodium (NA); potassium (K); calcium (CA); chloride (CL); phosphate (PHOS); bicarbonate (BICARB); and lactate dehydrogenase (LDH).

Urinalysis: A urinalysis test (dipstick) is performed for each participant. Urinary analysis is performed at Screening. If abnormality is noted for protein, blood, nitrite or leukocyte esterase (and at the discretion of the Investigator), a microscopic examination of red blood cells, white blood cells, bacteria and casts are performed. Macroscopic urinalysis parameters to be tested are: pH (PH); specific gravity (SPGRAV); creatinine (CREATININE); protein (PROT); glucose (GLUC); ketones (KETONES); total Bilirubin (BILI); occult Blood (OCCBLD); nitrite (NITRITE); urobilinogen (UROBIL); and leukocytes (WBC).

Viral serology: HBsAg, anti-HCV and HIV antibody testing are performed at Screening.

Urine drug screen and alcohol breath test: A urine drug screen is performed at Screening, prior to dosing on Day 1, and at the Day 7 Follow-up Visit. The urine drug screen includes but is not limited to cocaine, cannabinoids, amphetamines, benzodiazepines, opiates, tricyclic antidepressants, and methadone. An alcohol breath test is performed at Screening, prior to dosing on Day 1, and at the Day 7 Follow-up Visit.

Pregnancy testing and follicle-stimulating hormone testing: A serum pregnancy test is performed at the Screening visit for WOCBP only. A urine pregnancy test is performed prior to dosing on Day 1. If the result is positive, a serum test is performed for confirmation. Women not of childbearing potential must be postmenopausal (defined as cessation of regular menstrual periods for at least 12 months). Postmenopausal status is confirmed through testing of FSH levels ≥40 IU/mL at Screening.

Adverse and serious adverse events: AEs are reported for all participants from the time of consent until the completion of the Follow-up Visit. Serious adverse events are reported for all participants (enrolled and not enrolled) from the time of consent until the completion of the Follow-up Visit. Adverse events reported from the time of consent up until dosing are recorded as pre-treatment AEs. Treatment-emergent AEs (TEAEs) are evaluated from the first administration of IP until the Follow-up Visit or up to a 30-day follow-up period for AEs deemed related to treatment. Adverse events that are ongoing at the final follow-up are marked as Not Recovered/Not resolved on the AE eCRF page. All spontaneously volunteered and enquired for, as well as observed AEs, are recorded in the participant's medical records and the eCRF.

An AE is any event, side-effect, or other untoward medical occurrence that occurs in conjunction with the use of a medicinal product in humans, whether or not considered to have a causal relationship to this treatment. An AE can be any unfavorable and unintended sign that can include a clinically significant abnormal laboratory finding, symptom, or disease temporally associated with the use of a medicinal product, whether or not considered related to the medicinal product.

Events meeting the definition of an AE include: 1) exacerbation of a chronic or intermittent pre-existing condition including either an increase in frequency and/or intensity of the condition; 2) new conditions detected or diagnosed after IP administration that occur during the reporting periods, even though it may have been present prior to the start of the study; 3) signs, symptoms, or the clinical sequelae of a suspected interaction; and 4) signs, symptoms, or the clinical sequelae of a suspected overdose of either IP or concomitant medications (overdose per se is be reported as an AE/SAE)

Events that do not meet the definition of an AE include: 1) Medical or surgical procedure (e.g., endoscopy, appendectomy); the condition that leads to the procedure is reported as an AE if it meets the criteria of an AE; 2) situations where an untoward medical occurrence did not occur (e.g., social and/or convenience admission to a hospital); and 3) anticipated day-to-day fluctuations of pre-existing disease(s) or condition(s) present or detected at the start of the study that do not worsen. If there is evidence of an AE through report or observation, the Investigator or designee evaluates further and record the following information: time of onset and resolution; severity; seriousness; causality/relation to study treatment; action taken regarding IP; action taken regarding AE; and outcome. Only items scored as a "3" (severe) on the TNSS-M are reported as adverse events.

Severity of an adverse event: Severity of AEs is graded by the Investigator as one of: 1) Mild (Grade 1): A type of AE that is usually transient and may require only minimal treatment or therapeutic intervention. The event does not generally interfere with usual activities of daily living; 2) Moderate (Grade 2): A type of AE that is usually alleviated with additional specific therapeutic intervention. The event interferes with usual activities of daily living, causing discomfort but poses no significant or permanent risk of harm to the research participant; 3) Severe (Grade 3): A type of AE that interrupts usual activities of daily living, or significantly affects clinical status, or may require intensive therapeutic intervention; 4) Life-threatening (Grade 4): A type of AE that places the participant at immediate risk of death; and 5) Death (Grade 5): Events that result in death.

Causal relationship of an adverse event: The Investigator assesses the relationship between IP and the occurrence of each AE. The Investigator's assessment of the relationship of each AE to IP is recorded in the source documents and the eCRF. Alternative causes, such as medical history, concomitant therapy, other risk factors, and the temporal relationship of the event to the IP is considered and investigated, if appropriate. The following definitions are general guidelines to help assign grade of attribution: 1) Not related: The event is clearly related to other factors such as the participant's environment or clinical state, therapeutic interventions or concomitant drugs administered to the participant. This is especially so when an event occurs prior to the commencement of treatment with the IP; 2) Unlikely: The temporal association, participant history, and/or circumstances are such that the IP is not likely to have had an association with the observed event. Other conditions, including concurrent illness, progression, or expression of the disease state, or reaction to a concomitant drug administered appear to explain the event; 3) Possible: The event follows a reasonable temporal sequence from the time of IP administration or follows a known response to the IP but could have been produced by other factors such as the participant's clinical state, other therapeutic interventions, or concomitant drugs administered to the participant; 4) Probable: The event follows a reasonable temporal sequence from the time of IP administration and follows a known response to the IP and cannot be reasonably explained by other factors such as the participant's clinical state, other therapeutic interventions, or concomitant drugs administered to the participant; and 5) Definite: The event follows a reasonable temporal sequence from the time of IP administration or control abates upon discontinuation or cannot be explained by known characteristics of the participant's clinical state.

Expectedness: The MM is responsible for determining whether an AE is expected or unexpected. An AE is considered unexpected if the nature, severity, or frequency of the event is not consistent with risk information.

Outcome: Outcome of an AE is recorded on the AE eCRF as follows: recovered/resolved; recovering/resolving; recovered/resolved with sequelae; not recovered/not resolving; fatal; and unknown.

Definition of serious adverse event: An SAE is an AE occurring during any study phase (i.e. baseline, treatment, or follow-up), and at any dose of the IP, that fulfils one or more of the following: results in death; it is immediately life-threatening; it requires in-patient hospitalization or prolongation of existing hospitalization; it results in persistent or significant disability or incapacity; results in a congenital abnormality or birth defect; it is an important medical event that may jeopardize the participant or may require medical intervention to prevent one of the outcomes listed above. An AE is considered "life-threatening" if, in the opinion of either the Investigator or the Sponsor, the occurrence places the participant at immediate risk of death. It does not include an AE that, had it occurred in a more severe form, might have caused death.

Notification of a serious adverse event: All SAEs are reported within 24 hours from the time the site investigational team becomes aware of the event to meet requirements for expedited reporting of SAEs to applicable regulatory authorities and institutional ethics committees. Initial reporting is achieved by completing an SAE report form and email the assigned project email address, which is provided upon study setup. If completion of an SAE form and emailing is not possible, reporting by telephone is required and a completed SAE form must be emailed at the first opportunity. Initial notification of an SAE by telephone is confirmed in writing 24 hours from the time the site investigational team first becomes aware of the event using the SAE report form as described above. As further information regarding the SAE becomes available, such follow-up information is documented on a new SAE report form, marked as a follow-up report, scanned and emailed to the address at the bottom of the report form.

Withdrawal from the study in the event of an SAE and therapeutic measures taken are at the discretion of the Investigator. A full explanation for the discontinuation from the study are made in the participant's medical records and in the CRF. The Sponsor or their designee is responsible for notifying the relevant regulatory authorities of certain events. The Investigator is also be notified of all unexpected, serious, drug-related events that occur during the clinical trial. The investigational site is responsible for notifying its IRB/EC of these additional SAEs, if required.

Clinical Laboratory Abnormalities and Other Abnormal Assessments as Adverse Events and Serious Adverse Events: Abnormal laboratory findings (e.g. serum chemistry and hematology) or other abnormal assessments (e.g. ECG and vital signs) per se are not reported as AEs. However, those abnormal findings that are deemed clinically significant by the PI and/or delegate or are associated with signs and/or symptoms are recorded as AEs if they meet the definition of an AE (and recorded as an SAE if they meet the criteria of being serious) as previously described. Clinically significant abnormal laboratory or other abnormal findings that are detected after consent or that are present at baseline and worsen after consent are included as AEs (and SAEs if serious). The Investigator exercises medical and scientific judgement in deciding whether an abnormal laboratory finding, or other abnormal assessment is clinically significant. To be considered clinically significant, the abnormality is associated with a clinically evident sign or symptom or be likely to result in an evident sign or symptom in the near term. A clinically significant laboratory abnormality in the absence of clinical symptoms can jeopardize the participant and can require intervention to prevent immediate consequences. For example, a markedly low serum glucose concentration can not be accompanied by coma or convulsions yet be of a magnitude to require glucose administration to prevent such sequelae.

Recording adverse events: Adverse events spontaneously reported by the participant and/or in response to an open question from the study personnel or revealed by observation are recorded in accordance with the Investigator's normal clinical practice and on the AE page of the eCRF during the study at the investigational site. Abnormal values that constitute an SAE or lead to discontinuation of administration of IP must be reported and recorded as an AE. Information about AEs and SAEs are collected from the time of consent until the end of the study. The AE term are reported in standard medical terminology when possible. For each AE, the Investigator evaluates and reports the onset (date and time), resolution (date and time), intensity, causality, action taken, serious outcome (if applicable), and whether or not it caused the participant to discontinue the study. AEs that occur during the study are documented in the participant's medical record, on the AE eCRF and on the SAE report form. If an SAE report is completed, pertinent laboratory data is recorded on the SAE form, preferably with baseline values and copies of laboratory reports.

If the abnormal assessment meets the criteria for being serious, the SAE form is also be completed. A diagnosis, if known, or clinical signs or symptoms if the diagnosis is unknown, is used to complete the AE/SAE page. If no diagnosis is known and clinical signs or symptoms are not present, then abnormal finding is recorded.

Follow-up of Adverse Events and Serious Adverse Events: All AEs and SAEs that are deemed related, possibly related or probably related to the IP are followed until resolution, until the condition stabilizes, until the event is otherwise explained, or until the participant dies or is lost to follow-up. The Investigator is responsible for ensuring that follow-up includes any supplemental investigations as may be indicated to elucidate as completely as practical the nature and/or causality of the AE/SAE. Additional laboratory tests or investigations or consultation with other health care professionals are included. The Sponsor can request that the Investigator perform or arrange for the conduct of supplemental measurements and/or evaluations. If a participant dies during participation in the study or during a recognized follow-up period, the Sponsor is provided with a copy of any post-mortem findings, including histopathology.

Pregnancy: Pregnancy testing is performed in all WOCBP at Screening and Day 1 as per the Schedule of Assessments, and the pregnancy results is captured in the eCRF. All WOCBP re instructed to contact the Investigator immediately if they suspect they might be pregnant (e.g., missed or late menstrual period) at any time during the trial. Male participants contact the Investigator immediately if they suspect they may have fathered a child during the study treatment period. When possible, the partner's pregnancy is followed (to term) to determine the outcome. Should a pregnancy occur, the pregnancy must be reported and recorded on a Pregnancy Form. Pregnancy is not regarded as an AE unless there is a suspicion that the IP may have interfered with the effectiveness of a contraceptive medication. The Investigator reports the details on a Pregnancy Form to the Sponsor/assigned designee within 24 hours of knowledge of the pregnancy. Even though participants agree to withdraw or terminate the clinical trial, the Investigator follows-up and documents the process and results of all the pregnancies. If a male participant's female partner becomes pregnant while enrolled in the trial, a Pregnancy Form is completed and sent to the Clinical Research Organization (CRO) expeditiously, irrespective of whether the pregnancy meets the criteria for expedited reporting. Abortions (spontaneous, accidental, or therapeutic) are also reported. Congenital anomalies/birth defects always meet SAE criteria, and is therefore be expeditiously reported as an SAE, using the previously described process for SAE reporting. A Pregnancy Form is updated to reflect the outcome of the pregnancy. The Investigator reports any pregnancy (including pregnancy of a male participant's partner), even if no AE has occurred, on a Pregnancy Report Form within 24 hours of the Investigator becoming aware of the pregnancy.

Example 4: Single Ascending Dose Study

The single ascending dose study is conducted as a single-blind study with study participants blinded to treatment assignment. The radiologist providing review and interpretation of MRS studies is blinded to the treatment assignment, IP administered, MRS timing and other details of IP administration. Twenty subjects are randomized in a 1:1 fashion to one of two dosing cohorts.

IN NAC and IN GSH are administered using a Teleflex MAD device. Study medication, IN GSH 200 mg and IN NAC 100, 200, and 400 mg, are supplied in identical-appearing nasal administration devices. The dosing procedures are identical for the NAC and GSH 200 mg doses (0.5 mL once in each nostril). The dosing procedures are 0.25 mL in each nostril for the NAC 100 mg dose, and 0.5 ml twice in each nostril for the NAC 400 mg dose. The participants receive four successive doses of study medication with intervals of one week between each dose. The subject is otherwise be blinded to treatment assignment.

Twenty healthy volunteers are randomized in a 1:1 ratio to one of two regimens consisting of either low-dose IN NAC (100 mg) or IN GSH 200 mg, followed by sequential single escalating doses of IN NAC 200 mg and IN NAC 400 mg given at 7-day intervals on Days 8, 15 and 22 (TABLE 1). Cohort 1A receives IN GSH 200 mg, followed at one week intervals by successive doses of IN NAC 100 mg, IN NAC 200 mg and IN NAC 400 mg. Cohort 1B receives IN NAC 100 mg, followed at one week intervals by successive doses of IN GSH 200 mg, IN NAC 200 mg and IN NAC 400 mg. Both NAC and GSH ARE administered as 20% aqueous solutions. On each day of study medication dosing, MRS is performed, and blood samples are collected to determine peripheral blood concentrations of GSH, cysteine, free and total NAC, and RBG GSH/GSSG ratios prior to administering study medication, and at 1-, 3-, 6-, and 24-hours afterwards.

TABLE 1

| Cohort | Dose 1 | Dose 2 | Dose 3 | Dose 4 |
|---|---|---|---|---|
| 1A | GSH 200 mg | NAC 100 mg | NAC 200 mg | NAC 400 mg |
| 1B | NAC 100 mg | GSH 200 mg | NAC 200 mg | NAC 400 mg |

Change from baseline in the relative levels of NAC-derived neurometabolites are assessed following administration of a single dose of IN NAC or IN GSH followed at weekly intervals by single ascending doses of IN NAC, as well as changes in peripheral blood measurements of PK laboratories.

Participants are required to remain recumbent from the baseline scan through to the final 6-hour scan to the extent possible. Safety and tolerability are monitored, as outlined in TABLE 2. If tolerability is acceptable, Participants proceed to the next planned dose of study medication. Participants experiencing treatment-limiting adverse effects are discontinued from the study and do not proceed to the next dose. Participants return for a Follow-up Visit 7 days following the last dose of IP (Day 30+3 days) and receive a follow-up telephone call on Day 51 (+2 days) for safety assessment.

TABLE 2

| Activity | Screening visit[1] Day −28 to −1 | Dose 1 Day 1 | Doses 2, 3 and 4 Days 8, 15 and 22 | Post-Dosing Days 2, 9, 16 and 23 | Study Follow-up Visit Day 29 | Telephone call Day 50 |
|---|---|---|---|---|---|---|
| Informed consent | X | | | | | |
| Demography | X | | | | | |
| Eligibility criteria | X | X | X | | | |
| Medical/ medication history | X | | | | | |
| Drug/alcohol screen | X | X | X | | | |
| Laboratory tests[2] | X | | | | | |
| Randomization | | X | | | | |
| Physical exam | X | | | | X | |
| Brief physical exam | | X | X | X | | |

TABLE 2-continued

| Activity | Screening visit[1] Day −28 to −1 | Dose 1 Day 1 | Doses 2, 3 and 4 Days 8, 15 and 22 | Post-Dosing Days 2, 9, 16 and 23 | Study Follow-up Visit Day 29 | Telephone call Day 50 |
|---|---|---|---|---|---|---|
| Neurologic exam | X | | | | X | |
| Brief neurologic exam | | X | X | X | | |
| Height | X | | | | | |
| Weight | X | | | | X | |
| 12-lead ECG | X | | | X | X | |
| Laboratory tests[2] | | X | X | X | X | |
| Urinalysis | X | | | | | |
| VAS-tolerability | | X | X | X | X | |
| TNSS-M | X | X | X | X | X | X |
| Adverse Event Monitoring | X | X | X | X | X | X |
| Concomitant meds | X | X | X | X | X | X |
| IP dosing | | X | X | | | |
| Plasma GSH, cysteine, free and total NAC[3] | | X | X | X | | |
| RBC GSH/GSS[3] | | X | X | X | | |
| MRS[4] | | X | X | X | | |

ABBREVIATIONS: ECG, electrocardiogram; GSH, glutathione GSH/GSSG, reduced-to-oxidized glutathione; MRS, magnetic resonance spectroscopy; NAC, N-acetylcysteine; TNSS-M, Modified Total Nasal Symptom Scale; VAS-T, Visual Analog Scale for Tolerability
[1]Screening procedures must occur within 28 days of Day 1 IP dosing
[2]See Laboratory assessments for list of tests to be completed.
[3]Blood samples for NAC, cysteine, GSH and RBC GSH/GSSG drawn prior to each MR session.
[4]MRS pre-dose and 1, 3, 6 and 24 hours post-dose Example 5: Administration of Nose-to-Brain NAC A study in normal human volunteers with single and repeated intranasal (IN) delivery of commercially approved NAC doses and formulations is conducted using approved nasal delivery devices. Nose-to-brain delivery of existing NAC doses, formulations, and delivery devices are compared by determining the post-dose elevation levels in brain NAC and GSH. Elevation of brain NAC and GSH levels is determined at various time points and in various regions of the brain using magnetic resonance spectroscopy (MRS) (e.g., 1 hr, 3 hr, and 6 hr post-dosing). The delivery devices and formulations are configured to maximize the efficacy and tolerability of substance delivery to the brain, while avoiding dilution or elimination by the systemic circulation.

Different intranasal delivery devices are designed to delivery their cargo to one or more different regions of the nasal cavity. In some embodiments, an intranasal delivery device is designed to deliver cargo to the olfactory region innervated by the olfactory nerve. In some embodiments, an intranasal delivery device is designed to deliver cargo to the respiratory region innervated by the trigeminal nerve. In some embodiments, an intranasal delivery device is designed to deliver cargo to the cribiform plate punctuated by the rostral migratory stream pathway. In some embodiments, Experiments comparing the temporal and spatial pattern of delivery of NAC to the brain with different devices and/or device configurations is used to determine the anatomical pathway that is involved in drug delivery. In some embodiments, the anatomical pathway is the olfactory stream. In some embodiments, the anatomical pathway is the trigeminal stream. In some embodiments, the anatomical pathway is the rostral migratory stream. Experiments comparing the temporal and spatial pattern of delivery of NAC to the brain with different devices and/or device configurations is used to determine the cellular pathway that is involved in drug delivery. In some embodiments, the cellular pathway is an extracellular pathway. In some embodiments, the cellular pathway is a intracellular pathway. In some embodiments, the intracellular pathway is an intraneural pathway. In some embodiments, the intracellular pathway is a transcellular pathway. Upon determining the delivery pathway of a compound of the disclosure, devices and formulations can me modified to utilize the anatomical pathway or the cellular pathway and target specific regions of the brain affected by a brain disorder.

Figure 5:
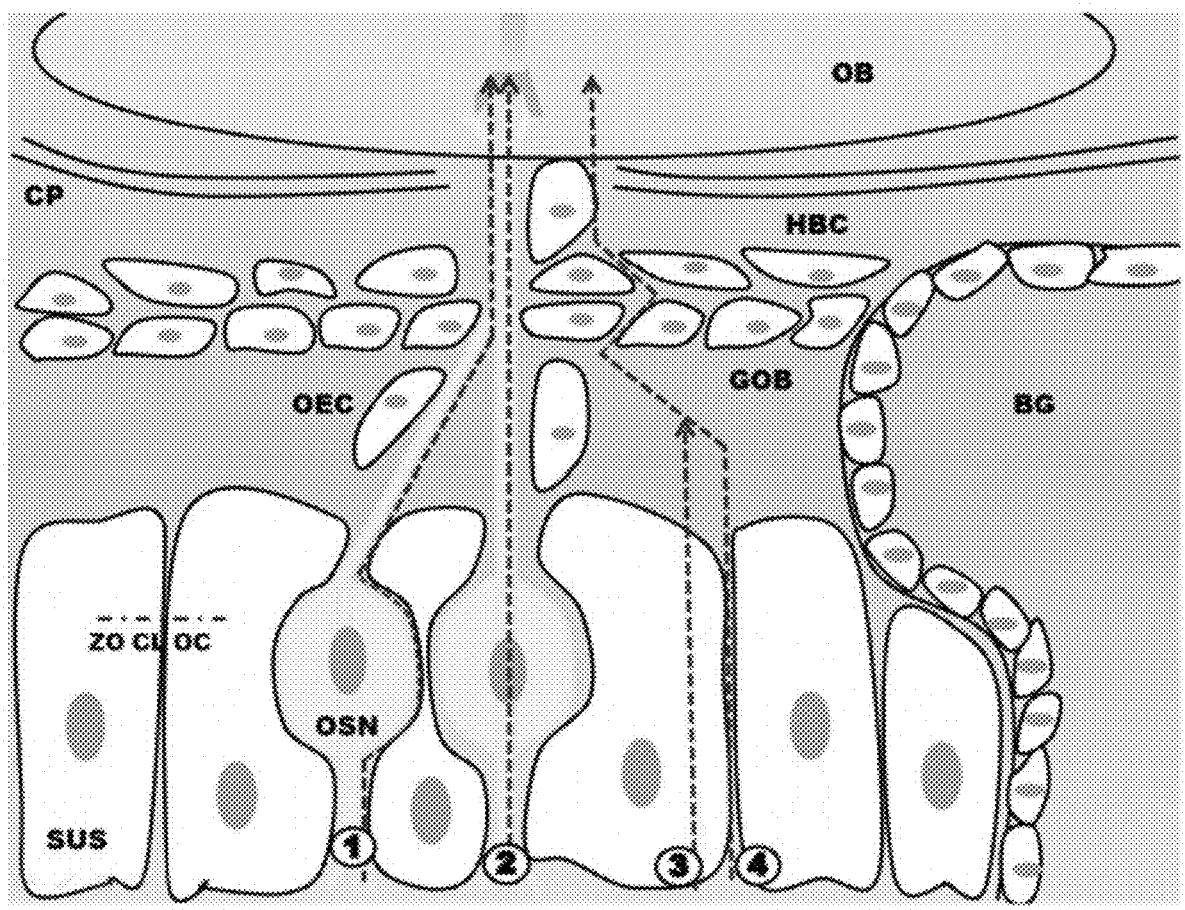
FIG. 5 illustrates that for each anatomical pathway, direct nose-to-brain delivery occurs by bulk flow alongside or around but outside cells (extracellular pathway), or by intracellular pathways through neurons, or across or along other supporting cells.

FIG. 5 illustrates that for each anatomical pathway, direct nose-to-brain delivery occurs by bulk flow alongside or around but outside cells (extracellular pathway), or by intracellular pathways through neurons, or across or along other supporting cells. Abbreviations: SUS: sustentacular cells; OSN: olfactory sensory neuron; OEC: olfactory ensheathing cell; GOB: globose basal cells; HBC: horizontal basal cells; BG: Bowman's gland; CP: cribriform plate; OB: olfactory bulb; ZO: zonula occludens; CL: claudin; OC: occludin.

The overall tolerability of IN NAC dosing is initially limited by the concentration of existing 10%-20% NAC aqueous solution formulations, tolerability of various IN volumes, and capacities of approved devices (e.g., Teleflex LMA® MAD Nasal Mucosal Atomizer, Aptar UDS/BDS, OptiNose breath-powered bi-directional device).

The rise in brain NAC+GSH levels is compared to two positive controls to measure assay sensitivity and PD: 1) increases in brain GSH levels produced by a well-tolerated standardized dose of IN GSH; or 2) the rise in NAC+GSH levels produced by a proven pharmacodynamically-(PD)-effective IV infusion of NAC. The effect of NAC on brain MRS NAC+GSH levels is calibrated against brain MRS NAC+GSH levels achieved by a repeated oral NAC dose regimen used to ameliorate post-blast concussive symptoms.

Single ascending IN doses of NAC are tested for brain NAC+GSH elevation capabilities by measuring brain GSH levels before administration of NAC. NAC+GSH levels at selective times following administration of test doses of IN NAC are measured, up to the maximum tolerated dose using available formulations and device combinations.

Pharmacokinetic (PK)/PD studies of brain GSH and GSH/glutathione disulfide (G-SSG) levels and brain drug exposure after ascending IN dosing of stable-labeled NAC in mice are designed to affirm that effective brain antioxidant protection occurs without excessive drug exposure. PK/PD studies of brain GSH and GSH/GSSG levels and brain NAC exposure after ascending IN dosing of stable-labeled NAC are replicated in non-human primate species. Results from non-human primate species studies are used to predict human nose-to-brain delivery. A human PD study is selected to determine IN NAC dosing and formulations yielding NAC+GSH levels that replicate or exceed the brain GSH levels (measured by non-invasive MRS) of the IN GSH delivery and/or the NAC+GSH levels of the successful oral NAC regimen in post-blast concussion in normal human volunteers.

The PD-effective IN NAC doses are taken into a study in subjects with blast exposure and/or other subjects experiencing mTBI using agreed-upon clinical study outcomes and additional accepted and validated clinical endpoints. Ancillary studies are incorporated into the study. The ancillary studies employ MRS to image standardized regions of the brain or regions of the brain related to mTBI injuries to determine GSH levels or other putative biomarkers, such as elevated glutamate levels before NAC treatment, and NAC+GSH levels during and after IN NAC treatment.

Example 6: Administration of Nose-to-Brain GSH

GSH administration into the nasal cavity to promote nose-to-brain delivery is systematically altered and fine-tuned to deliver GSH to specific regions within the nasal cavity. One or more of the nose-to-brain transfer routes are utilized.

Specialized nasal delivery devices that can accommodate different particle or droplet sizes, possess variable plume characteristics, and can control anatomical distribution within the nasal cavity are used for intranasal GSH administration. Using the specialized nasal delivery devices, a range of GSH formulations are administered to promote and enhance bioavailability within specific regions of the nasal cavity to improve or target GSH delivery to specific regions of the CNS. GSH formulations are optimized for biocompatibility, tolerability, volume, stability, ease of use, and production cost of the drug/formulation/device combination.

GSH levels in the brain upon administration of the GSH formulations of the disclosure are measured 1 hr, 3 hr, and 6 hr post-dosing. The delivery devices and formulations are configured to maximize the efficacy and tolerability of substance delivery to the brain, while avoiding dilution or elimination by the systemic circulation. GSH is administered in healthy human volunteers and patients with neurological diseases, such as concussion or Parkinson's Disease.

Example 7: Measuring Nose-to-Brain NAC or GSH Delivery Using Magnetic Resonance Spectroscopy Nose-to-brain NAC or GSH delivery is quantified and measured in healthy human volunteers and patients with neurological diseases, such as concussion or Parkinson's Disease. NAC or GSH is administered intranasally to subjects free of neurological disease or structural defects in the brain to various regions of the nasal cavity. The uptake of intranasal NAC or GSH in healthy subjects is assessed using magnetic resonance imaging (MRI). Magnetic resonance spectroscopy (MRS) is used to measure NAC or GSH delivery to specific regions of the brain with detailed temporo-spatial mapping. Regional brain GSH is measured at several times after dosing to demonstrate the regional and temporal pattern of intranasal-NAC-derived GSH elevation in regions of the CNS.

Nose-to-brain GSH is used as a control. GSH levels in the brain upon administration of the NAC or GSH formulations of the disclosure are measured 1 hr, 3 hr, and 6 hr post-dosing.

Based on preliminary results, pharmacodynamic (PD) regional and temporal profiles of NAC-derived GSH within brain structures are characterized with respect to dose, formulation, and regional delivery within the nasal cavity after single and repeated doses.

Example 8: Administration of Intranasal Nose-to-Brain NAC to a Subject with a Military-Related Traumatic Brain Injury A soldier with a military-related head injury from resulting from combat is provided with a pharmaceutical composition comprising 20% aqueous NAC. The formulation is administered intranasally and provides nose-to-brain delivery of NAC. 0.25 mL of the NAC formulation is administered per nostril of the subject (total 0.5 mL) using a Teleflex LMA® MAD Nasal™ Intranasal mucisal atomization device.

The uptake of intranasal NAC in the soldier is assessed using MRS in specific regions of the brain with detailed temporo-spatial mapping. Regional brain GSH is measured at several times after dosing to demonstrate the regional and temporal pattern of intranasal-NAC-derived GSH elevation in regions of the CNS.

EMBODIMENTS

The following non-limiting embodiments provide illustrative examples of the invention, but do not limit the scope of the invention.

Embodiment 1. A method of treating a brain disorder in a brain of a subject in need thereof, the method comprising intranasally administering to afm nose of the subject a dose of N-acetylcysteine (NAC), or a congener thereof, wherein the intranasal administration provides a therapeutically-effective amount of the NAC, or the congener thereof, to the brain from the nose, and wherein the subject is not substantially systemically exposed to the NAC, or the congener thereof, upon the intranasal administration.

Embodiment 2. The method of embodiment 1, wherein the brain disorder is a concussion.

Embodiment 3. The method of embodiment 1, wherein the brain disorder is post-concussion syndrome.

Embodiment 4. The method of embodiment 1, wherein the brain disorder is a mild traumatic brain injury.

Embodiment 5. The method of embodiment 1, wherein the brain disorder is a traumatic brain injury.

Embodiment 6. The method of embodiment 1, wherein the brain disorder is associated with athletic activity.

Embodiment 7. The method of embodiment 1, wherein the brain disorder is a neurodegenerative disease.

Embodiment 8. The method of embodiment 1, wherein the brain disorder is dementia.

Embodiment 9. The method of embodiment 1, wherein the brain disorder is age-related.

Embodiment 10. The method of embodiment 1, wherein the brain disorder is Parkinson's disease.

Embodiment 11. The method of embodiment 1, wherein the brain disorder is a stroke.

Embodiment 12. The method of any one of embodiments 1-11, wherein the congener is glutathione (GSH).

Embodiment 13. The method of any one of embodiments 1-12, wherein substantially all of the dose enters the brain without crossing a blood brain barrier of the subject.

Embodiment 14. The method of any one of embodiments 1-13, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

Embodiment 15. The method of any one of embodiments 1-13, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC enters the brain.

Embodiment 16. The method of any one of embodiments 1-13, wherein the NAC, or the congener thereof, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the brain.

Embodiment 17. The method of any one of embodiments 1-16, wherein the therapeutically-effective amount is about 1 mg/kg to about 10 mg/kg.

Embodiment 18. The method of any one of embodiments 1-17, wherein the therapeutically-effective amount is from about 100 mg to about 400 mg.

Embodiment 19. The method of any one of embodiments 1-18, wherein the dose is administered using a nasal pump.

Embodiment 20. The method of any one of embodiments 1-19, wherein the dose is administered using an atomizer.

Embodiment 21. The method of any one of embodiments 1-19, wherein the dose is administered using a nebulizer.

Embodiment 22. The method of any one of embodiments 1-21, wherein substantially all of the dose enters a nasal cavity of the subject.

Embodiment 23. A method of treating a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein substantially all of the NAC, or the congener thereof, enters the brain without crossing a blood brain barrier of the subject.

Embodiment 24. The method of embodiment 23, wherein the brain disorder is a concussion.

Embodiment 25. The method of embodiment 23, wherein the brain disorder is post-concussion syndrome.

Embodiment 26. The method of embodiment 23, wherein the brain disorder is a mild traumatic brain injury.

Embodiment 27. The method of embodiment 23, wherein the brain disorder is a traumatic brain injury.

Embodiment 28. The method of embodiment 23, wherein the brain disorder is a neurodegenerative disease.

Embodiment 29. The method of embodiment 23, wherein the brain disorder is associated with athletic activity.

Embodiment 30. The method of embodiment 23, wherein the brain disorder is dementia.

Embodiment 31. The method of embodiment 23, wherein the brain disorder is age-related.

Embodiment 32. The method of embodiment 23, wherein the brain disorder is Parkinson's disease.

Embodiment 33. The method of embodiment 23, wherein the brain disorder is a stroke.

Embodiment 34. The method of any one of embodiments 23-33, wherein the congener is glutathione (GSH).

Embodiment 35. The method of any one of embodiments 23-34, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

Embodiment 36. The method of any one of embodiments 23-34, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters a cerebral spinal fluid of the subject, and then the NAC enters the brain.

Embodiment 37. The method of any one of embodiments 23-34, wherein the NAC, or the congener thereof, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the brain.

Embodiment 38. The method of any one of embodiments 23-37, wherein the therapeutically-effective amount is about 1 mg/kg to about 10 mg/kg.

Embodiment 39. The method of any one of embodiments 23-38, wherein the therapeutically-effective amount is from about 100 mg to about 400 mg.

Embodiment 40. The method of any one of embodiments 23-39, wherein the dose is administered using a nasal pump.

Embodiment 41. The method of any one of embodiments 23-39, wherein the dose is administered using an atomizer.

Embodiment 42. The method of any one of embodiments 23-39, wherein the dose is administered using a nebulizer.

Embodiment 43. The method of any one of embodiments 23-42, wherein substantially all of the dose enters a nasal cavity of the subject.

Embodiment 44. A method of treating a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

Embodiment 45. The method of embodiment 44, wherein the brain disorder is a concussion.

Embodiment 46. The method of embodiment 44, wherein the brain disorder is post-concussion syndrome.

Embodiment 47. The method of embodiment 44, wherein the brain disorder is a mild traumatic brain injury.

Embodiment 48. The method of embodiment 44, wherein the brain disorder is a traumatic brain injury.

Embodiment 49. The method of embodiment 44, wherein the brain disorder is a neurodegenerative disease.

Embodiment 50. The method of embodiment 44, wherein the brain disorder is associated with athletic activity.

Embodiment 51. The method of embodiment 44, wherein the brain disorder is dementia.

Embodiment 52. The method of embodiment 44, wherein the brain disorder is age-related.

Embodiment 53. The method of embodiment 44, wherein the brain disorder is Parkinson's disease.

Embodiment 54. The method of embodiment 44, wherein the brain disorder is a stroke.

Embodiment 55. The method of any one of embodiments 44-54, wherein the congener is glutathione (GSH).

Embodiment 56. The method of any one of embodiments 44-55, wherein substantially all of the dose enters the brain without crossing a blood brain barrier of the subject.

Embodiment 57. The method of any one of embodiments 44-56, wherein the therapeutically-effective amount is about 1 mg/kg to about 10 mg/kg.

Embodiment 58. The method of any one of embodiments 44-57, wherein the therapeutically-effective amount is from about 100 mg to about 400 mg.

Embodiment 59. The method of any one of embodiments 44-58, wherein the dose is administered using a nasal pump.

Embodiment 60. The method of any one of embodiments 44-58, wherein the dose is administered using an atomizer.

Embodiment 61. The method of any one of embodiments 44-58, wherein the dose is administered using a nebulizer.

Embodiment 62. The method of any one of embodiments 44-61, wherein substantially all of the dose enters a nasal cavity of the subject.

Embodiment 63. A method of treating a brain disorder in a brain of a subject in need thereof, the method comprising intranasally administering to a nose of the subject a dose of N-acetylcysteine (NAC), or a congener thereof, wherein the intranasal administration provides a therapeutically-effective amount of the NAC, or the congener thereof, to the brain from the nose, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

Embodiment 64. The method of embodiment 63, wherein the brain disorder is a concussion.

Embodiment 65. The method of embodiment 63, wherein the brain disorder is post-concussion syndrome.

Embodiment 66. The method of embodiment 63, wherein the brain disorder is a mild traumatic brain injury.

Embodiment 67. The method of embodiment 63, wherein the brain disorder is a traumatic brain injury.

Embodiment 68. The method of embodiment 63, wherein the brain disorder is a neurodegenerative disease.

Embodiment 69. The method of embodiment 63, wherein the brain disorder is associated with athletic activity.

Embodiment 70. The method of embodiment 63, wherein the brain disorder is dementia.

Embodiment 71. The method of embodiment 63, wherein the brain disorder is age-related.

Embodiment 72. The method of embodiment 63, wherein the brain disorder is Parkinson's disease.

Embodiment 73. The method of embodiment 63, wherein the brain disorder is a stroke.

Embodiment 74. The method of any one of embodiments 63-73, wherein the congener is glutathione (GSH).

Embodiment 75. The method of any one of embodiments 63-74, wherein substantially all of the dose enters a nasal cavity of the subject.

Embodiment 76. The method of any one of embodiments 63-75, wherein the therapeutically-effective amount is about 1 mg/kg to about 10 mg/kg.

Embodiment 77. The method of any one of embodiments 63-76, wherein the therapeutically-effective amount is from about 100 mg to about 400 mg.

Embodiment 78. The method of any one of embodiments 63-77, wherein the dose is administered using a nasal pump.

Embodiment 79. The method of any one of embodiments 63-77, wherein the dose is administered using an atomizer.

Embodiment 80. The method of any one of embodiments 63-77, wherein the dose is administered using a nebulizer.

Embodiment 81. The method of any one of embodiments 63-80, wherein substantially all of the dose enters a nasal cavity of the subject.

Embodiment 82. A method of treating a brain disorder in a brain of a subject in need thereof, the method comprising intranasally administering to a nose of the subject N-acetylcysteine (NAC), or a congener thereof, wherein the intranasal administration provides a therapeutically-effective amount of the NAC, or the congener thereof, to the brain from the nose, wherein the NAC, or the congener thereof, crosses a respiratory epithelium of the subject after the intranasal administration, and then after crossing the respiratory epithelium, the NAC crosses a trigeminal nerve of the subject, and then after crossing the trigeminal nerve, then NAC enters the brain.

Embodiment 83. The method of embodiment 82, wherein the brain disorder is a concussion.

Embodiment 84. The method of embodiment 82, wherein the brain disorder is post-concussion syndrome.

Embodiment 85. The method of embodiment 82, wherein the brain disorder is a mild traumatic brain injury.

Embodiment 86. The method of embodiment 82, wherein the brain disorder is a traumatic brain injury.

Embodiment 87. The method of embodiment 82, wherein the brain disorder is a neurodegenerative disease.

Embodiment 88. The method of embodiment 82, wherein the brain disorder is associated with athletic activity.

Embodiment 89. The method of embodiment 82, wherein the brain disorder is dementia.

Embodiment 90. The method of embodiment 82, wherein the brain disorder is age-related.

Embodiment 91. The method of embodiment 82, wherein the brain disorder is Parkinson's disease.

Embodiment 92. The method of embodiment 82, wherein the brain disorder is a stroke.

Embodiment 93. The method of any one of embodiments 82-92, wherein the congener is glutathione (GSH).

Embodiment 94. The method of any one of embodiments 82-93, wherein substantially all of the dose enters a nasal cavity of the subject.

Embodiment 95. The method of any one of embodiments 82-94, wherein the therapeutically-effective amount is about 1 mg/kg to about 10 mg/kg.

Embodiment 96. The method of any one of embodiments 82-95, wherein the therapeutically-effective amount is from about 100 mg to about 400 mg.

Embodiment 97. The method of any one of embodiments 82-96, wherein the dose is administered using a nasal pump.

Embodiment 98. The method of any one of embodiments 82-96, wherein the dose is administered using an atomizer.

Embodiment 99. The method of any one of embodiments 82-96, wherein the dose is administered using a nebulizer.

Embodiment 100. The method of any one of embodiments 82-99, wherein substantially all of the dose enters a nasal cavity of the subject.

What is claimed is:

1. A method of treating a brain disorder in a brain of a subject in need thereof, the method comprising intranasally administering to a nose of the subject a dose of N-acetyl-cysteine (NAC), or a congener thereof, wherein the intranasal administration provides a therapeutically-effective amount of the NAC, or the congener thereof, from the nose of the subject to one or more selective regions of the brain involved in the brain disorder, and wherein to reach the one or more selective regions of the brain upon the intranasal administration, a first portion of the dose is transported through an olfactory pathway of the subject and a second portion of the does is transported through a trigeminal pathway of the subject.

2. The method of claim 1, wherein the brain disorder is a concussion.

3. The method of claim 1, wherein the brain disorder is post-concussion syndrome.

4. The method of claim 1, wherein the brain disorder is a mild traumatic brain injury.

5. The method of claim 1, wherein the brain disorder is a traumatic brain injury.

6. The method of claim 1, wherein the brain disorder is associated with athletic activity.

7. The method of claim 1, wherein the brain disorder is a neurodegenerative disease.

8. The method of claim 1, wherein the brain disorder is dementia.

9. The method of claim 1, wherein the brain disorder is age-related.

10. The method of claim 1, wherein the brain disorder is Parkinson's disease.

11. The method of claim 1, wherein the brain disorder is a stroke.

12. The method of claim 1, wherein the congener is glutathione (GSH).

13. The method of claim 1, wherein substantially all of the dose enters the brain without crossing a blood brain barrier of the subject.

14. The method of claim 1, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the brain.

15. The method of claim 1, wherein the NAC, or the congener thereof, crosses an olfactory epithelium of the subject after the intranasal administration, and then after crossing the olfactory epithelium, the NAC, or the congener thereof, enters an olfactory nerve of the subject, and then after crossing the olfactory nerve, the NAC, or the congener thereof, enters the cerebral spinal fluid of the subject, and then the NAC, or the congener thereof, enters the brain.

16. The method of claim 1, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the brain.

17. The method of claim 1, wherein the therapeutically-effective amount is about 1 mg/kg to about 10 mg/kg.

18. The method of claim 17, wherein the therapeutically-effective amount is from about 100 mg to about 400 mg.

19. The method of claim 1, wherein the dose is administered using a nasal pump.

20. The method of claim 1, wherein the dose is administered using an atomizer.

21. The method of claim 1, wherein the dose is administered using a nebulizer.

22. The method of claim 1, wherein substantially all of the dose enters a nasal cavity of the subject.

23. The method of claim 1, wherein the first portion is about 1% to 99% of the dose and the second portion is about 99% to 1% of the dose.

24. The method of claim 1, wherein the NAC, or the congener thereof, crosses a respiratory epithelium of the subject after the intranasal administration, and then after crossing the respiratory epithelium, the NAC, or the congener thereof, crosses a trigeminal nerve of the subject, and then after crossing the trigeminal nerve, then the NAC, or the congener thereof, enters the cerebrospinal fluid of the subject, and then the NAC, or the congener thereof, enters the brain.

* * * * *

UNITED STATES PATENT AND TRADEMARK OFFICE
CERTIFICATE OF CORRECTION

| | |
|---|---|
| PATENT NO. | : 12,090,130 B2 |
| APPLICATION NO. | : 17/127075 |
| DATED | : September 17, 2024 |
| INVENTOR(S) | : Douglas A. Greene et al. |

Page 1 of 1

It is certified that error appears in the above-identified patent and that said Letters Patent is hereby corrected as shown below:

In the Specification

Column 47, Line 51, change "delivery" to --deliver--;
Column 50, Line 55, change "administering to afm nose" to --administering to a nose--;

In the Claims

Claim 1, Column 55, Line 31, change "portion of the does" to --portion of the dose--.

Signed and Sealed this
Fifth Day of November, 2024

Katherine Kelly Vidal
*Director of the United States Patent and Trademark Office*